United States Patent
Thompson et al.

(10) Patent No.: US 12,419,715 B2
(45) Date of Patent: Sep. 23, 2025

(54) MASTER CONTROL DEVICE WITH MULTI-FINGER GRIP AND METHODS THEREFOR

(71) Applicant: Intuitive Surgical Operations, Inc., Sunnyvale, CA (US)

(72) Inventors: Allen C. Thompson, Los Altos, CA (US); Robert B. Hubler, Woodinville, WA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1362 days.

(21) Appl. No.: 16/764,349

(22) PCT Filed: Nov. 14, 2018

(86) PCT No.: PCT/US2018/061031
§ 371 (c)(1),
(2) Date: May 14, 2020

(87) PCT Pub. No.: WO2019/099504
PCT Pub. Date: May 23, 2019

(65) Prior Publication Data
US 2020/0275985 A1    Sep. 3, 2020

Related U.S. Application Data

(60) Provisional application No. 62/586,768, filed on Nov. 15, 2017.

(51) Int. Cl.
*A61B 34/00* (2016.01)
*A61B 34/20* (2016.01)
(Continued)

(52) U.S. Cl.
CPC .............. *A61B 34/74* (2016.02); *A61B 34/20* (2016.02); *A61B 34/35* (2016.02); *A61B 34/37* (2016.02);
(Continued)

(58) Field of Classification Search
None
See application file for complete search history.

(56) References Cited

U.S. PATENT DOCUMENTS 3,350,956 A    11/1967   Barton et al.
5,176,696 A    1/1993    Saunders
(Continued)

FOREIGN PATENT DOCUMENTS

EP    3015081 A1    5/2016
EP    3245975 A1    11/2017
(Continued)

OTHER PUBLICATIONS

International Preliminary Report on Patentability for Application No. PCT/US2018/061031, mailed on May 19, 2020, 13 pages.
(Continued)

*Primary Examiner* — Gary Jackson
*Assistant Examiner* — Anant A Gupta
(74) *Attorney, Agent, or Firm* — IP Spring

(57) ABSTRACT

Implementations relate to a master control device. In some implementations, a master control device includes a thumb grip member including a thumb grip receptive to a thumb of a hand of a user. The master control device includes a finger grip member coupled to the thumb grip member at a proximal end of the master control device and extending toward a distal end of the master control device, where the finger grip member includes a finger grip receptive to multiple fingers of the hand. The thumb grip member and finger grip member are movable in a pinching configuration
(Continued)

with respect to each other. The master control device includes a sensor coupled to at least one of the thumb grip member or finger grip member to sense relative positions of the thumb grip member and finger grip member with respect to each other in the pinching configuration.

20 Claims, 11 Drawing Sheets

(51) Int. Cl.
  *A61B 34/35* (2016.01)
  *A61B 34/37* (2016.01)
  *A61B 17/00* (2006.01)
  *G05G 9/047* (2006.01)

(52) U.S. Cl.
  CPC ............... *A61B 2017/00424* (2013.01); *A61B 2034/2048* (2016.02); *A61B 2034/2051* (2016.02); *A61B 2034/2055* (2016.02); *A61B 2034/2059* (2016.02); *A61B 2034/2061* (2016.02); *A61B 2034/2063* (2016.02); *A61B 2034/2065* (2016.02); *A61B 2034/741* (2016.02); *A61B 2034/742* (2016.02); *G05G 9/047* (2013.01); *G05G 2009/0474* (2013.01); *G05G 2009/04774* (2013.01)

(56) References Cited

U.S. PATENT DOCUMENTS

| | | | |
|---|---|---|---|
| 5,410,638 A * | 4/1995 | Colgate | A61B 34/70 700/262 |
| 5,876,325 A | 3/1999 | Mizuno et al. | |
| 5,976,121 A | 11/1999 | Matern et al. | |
| 6,089,106 A | 7/2000 | Patel et al. | |
| 8,016,818 B2 | 9/2011 | Ellis et al. | |
| 8,521,331 B2 | 8/2013 | Itkowitz | |
| 8,638,057 B2 | 1/2014 | Goldberg et al. | |
| 2008/0262538 A1 | 10/2008 | Danitz et al. | |
| 2009/0030428 A1 | 1/2009 | Omori et al. | |
| 2010/0069940 A1 | 3/2010 | Miller et al. | |
| 2010/0080669 A1 | 4/2010 | Labonville et al. | |
| 2010/0228156 A1 | 9/2010 | Valero-Cuevas et al. | |
| 2011/0118748 A1 * | 5/2011 | Itkowitz | A61B 90/98 606/130 |
| 2011/0118753 A1 | 5/2011 | Itkowitz et al. | |
| 2011/0208000 A1 | 8/2011 | Honda et al. | |
| 2012/0041595 A1 | 2/2012 | Greeley et al. | |
| 2013/0035697 A1 | 2/2013 | Ogawa et al. | |
| 2014/0018960 A1 | 1/2014 | Itkowitz | |
| 2014/0160015 A1 | 6/2014 | Ogawa et al. | |
| 2014/0165770 A1 | 6/2014 | Abri et al. | |
| 2014/0276646 A1 | 9/2014 | Wong et al. | |
| 2015/0073340 A1 | 3/2015 | Pacheco et al. | |
| 2015/0290814 A1 | 10/2015 | Schiele et al. | |
| 2016/0202134 A1 | 7/2016 | Malackowski et al. | |
| 2016/0216167 A1 | 7/2016 | Blumenkranz et al. | |
| 2017/0095298 A1 | 4/2017 | Vakharia et al. | |
| 2017/0296280 A1 | 10/2017 | Ogawa et al. | |
| 2018/0147019 A1 * | 5/2018 | Farritor | A61B 34/30 |
| 2018/0168758 A1 * | 6/2018 | Lutzow | A61B 34/30 |
| 2020/0289216 A1 | 9/2020 | Denlinger et al. | |
| 2020/0390510 A1 | 12/2020 | Thompson et al. | |
| 2021/0298855 A1 | 9/2021 | Thompson et al. | |

FOREIGN PATENT DOCUMENTS

| | | | |
|---|---|---|---|
| JP | 2006321027 A | 11/2006 | |
| WO | WO-2012127404 A2 * | 9/2012 | ............ A61B 34/70 |
| WO | WO-2013018933 A1 | 2/2013 | |
| WO | WO-2016154173 A1 | 9/2016 | |
| WO | WO-2016201544 A1 | 12/2016 | |
| WO | WO-2017031132 A1 | 2/2017 | |
| WO | WO-2019099584 A1 | 5/2019 | |
| WO | WO-2019217882 A1 | 11/2019 | |

OTHER PUBLICATIONS

International Preliminary Report on Patentability for Application No. PCT/US2018/061143, mailed on May 28, 2020, 15 pages.
International Preliminary Report on Patentability for Application No. PCT/US2019/031813, mailed on Nov. 26, 2020, 10 pages.
International Search Report and Written Opinion for Application No. PCT/US2018/061143, mailed on Apr. 15, 2019, 22 pages.
International Search Report and Written Opinion for Application No. PCT/US2019/031813, mailed on Aug. 14, 2019, 13 pages.
International Search Report and Written Opinion for Application No. PCT/US2018/061031, mailed on Apr. 15, 2019, 19 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP18879759.1, mailed on Nov. 11, 2021, 13 pages.
Extended European Search Report for Application No. EP18878247.8 mailed on Jul. 9, 2021. 10 pages.

* cited by examiner

700

MASTER CONTROL DEVICE WITH MULTI-FINGER GRIP AND METHODS THEREFOR

CROSS-REFERENCE TO RELATED APPLICATIONS

The present application is a U.S. National Phase application of International Patent Application No. PCT/US2018/061031, filed Nov. 14, 2018 and titled "Master Control Device with Multi-finger Grip and Methods Therefor," which claims priority to U.S. Provisional Patent Application No. 62/586,768, filed Nov. 15, 2017 and titled "Master Control Device with Multi-finger Grip and Method Therefor," the entire contents of both of which are hereby incorporated by reference.

BACKGROUND

In teleoperated operations such as teleoperated surgery, a user typically operates a master controller, e.g., included in a workstation or console, to remotely control (e.g., teleoperate) the motion and functions of instruments at a work site (e.g., surgical site). The master controller utilizes master controls, which will typically include one or more hand input devices such as pincher grips, joysticks, exo-skeletal gloves, or the like. These hand input devices are in communication with the controlled instrument. More specifically, a manipulator or "slave" device including the instrument is moved based on the user's manipulation of the hand input devices. In some examples of a surgical or other medical operation, a hand input device may control, via the teleoperated surgery system, a variety of surgical instruments such as tissue graspers, needle drivers, electrosurgical cautery probes, cameras, etc. Each of these instruments performs functions for the surgeon, for example, holding or driving a needle, grasping a blood vessel, or dissecting, cauterizing, or coagulating tissue.

For some hand input devices, the user may have difficulty manipulating a hand input device, e.g., over long periods of time, while maintaining a secure grip on the hand input device. Further, in some situations, it may be beneficial to operate the hand input device without being bound to a stationary workstation or console.

SUMMARY

Implementations of the present application relate to a master control device with a multi-finger grip and methods for using such a control device. In some implementations, a master control device includes a thumb grip member including a thumb grip receptive to a thumb of a hand of a user. The master control device also includes a finger grip member coupled to the thumb grip member at a proximal end of the master control device and extending toward a distal end of the master control device. The finger grip member includes a finger grip receptive to multiple fingers of the hand of the user. The thumb grip member and the finger grip member are movable in a pinching configuration with respect to each other. The master control device includes a sensor coupled to the thumb grip member and/or the finger grip member and configured to sense relative positions of the thumb grip member and the finger grip member with respect to each other in the pinching configuration.

With further regard to the master control device, in some implementations, the master control device is a surgical system master control device configured to provide control signals to a surgical teleoperated system. In some implementations, the master control device further includes a sensor configured to detect a position and/or an orientation of the master control device in a working environment of the master control device. In some implementations, the finger grip member is configured to receive the multiple fingers positioned adjacent to each other.

In some implementations, the thumb grip member and the finger grip member are coupled at the proximal end to form a U-shaped unitary piece in which the thumb grip member and the finger grip member are configured to be moved toward or away from each other in the pinching configuration. In some implementations, the thumb grip member and the finger grip member are separate members that are rotatably coupled to each other at a proximal end of the master control device. In some implementations, the thumb grip member is movable in a first degree of freedom and the finger grip member is movable in a second degree of freedom, and the sensor is configured to sense respective positions of the thumb grip member and the finger grip member in the first degree of freedom and the second degree of freedom.

In some implementations, the finger grip member includes a finger grip extension portion that extends from the finger grip in a direction away from the thumb grip member, where the finger grip extension portion is positioned between the multiple fingers and one or more other fingers of the hand. In some implementations, the finger grip member includes a finger grip extension portion that is configured to be contacted by a third finger of the hand on a first side (e.g., grip side) of the finger grip extension portion, and configured to be contacted by a second finger of the hand on a second side of the finger grip extension portion. In some implementations, the finger grip extension portion extends at least partially around at least one finger of the multiple fingers of the hand and is configured to support the master control device on the multiple fingers of the hand during operation of the master control device. For example, such a finger grip extension portion enables the thumb to be disengaged from the thumb grip member during the operation of the master control device, and a sensor of the master control device that is coupled to the thumb grip member is configured to detect disengagement of the thumb from the thumb grip member and provide a sensor signal in response to the disengagement, e.g., allowing control of different system functions based on thumb engagement.

In some implementations, the master control device includes an input control coupled to the finger grip member on a second side of the finger grip member that is opposite to a first side of the finger grip member that includes a finger grip surface engaged by the multiple fingers. In some implementations, the master control device further includes a central extension member coupled to the finger grip member and extending from the finger grip member toward the thumb grip member, and an input control provided on a surface of the central extension member between the finger grip member and the thumb grip member. In some implementations, the thumb grip member includes a thumb grip extension portion that extends from the thumb grip member in a direction away from the finger grip member. In some implementations, the master control device further includes an input control coupled to the thumb grip member, e.g., on a second side of the thumb grip member that is opposite to a first side of the thumb grip member that is engaged by the thumb. In some implementations, the master control device further includes a control wheel positioned between the thumb grip member and the finger grip member, where the control wheel is coupled to one of the thumb grip member and the finger grip member.

In some implementations, a master control system includes a master device that includes a thumb grip member including a thumb grip receptive to a thumb of a hand of a user. The master device also includes a finger grip member coupled to the thumb grip member at a proximal end of the master device and extending approximately in parallel to the thumb grip member toward a distal end of the master device, where the finger grip member includes a finger grip configured to receive multiple fingers of the hand of the user, and where the thumb grip member and the finger grip member are movable in a pinching configuration with respect to each other. The master device also includes a sensor coupled to the thumb grip member and/or the finger grip member and configured to sense relative positions of the thumb grip member and the finger grip member with respect to each other in the pinching configuration. The master device also includes a control device coupled to a slave device and configured to provide control signals to the slave device while a master-slave control relationship is established between the master device and the slave device, where the control device is configured to maintain the master-slave control relationship while the master device is moved by the user in a working environment.

With further regard to the master control system, in some implementations, the finger grip member is configured to engage the multiple fingers that are positioned adjacent to each other. In some implementations, the thumb grip member and the finger grip member are coupled at the proximal end to form a U-shaped unitary piece in which the thumb grip member and the finger grip member are configured to be moved toward and away from each other in the pinching configuration. In some implementations, the thumb grip member and the finger grip member are separate members, and wherein the thumb grip member and the finger grip member are rotatably coupled to each other at a proximal end of the master device.

In some implementations, the finger grip member includes a finger grip extension portion that extends from the finger grip member in a direction away from the thumb grip member, where the finger grip extension portion is positioned between the multiple fingers and one or more other fingers of the hand. In some implementations, the thumb grip member includes a thumb grip extension portion that extends from the thumb grip member in a direction away from the finger grip member, and an input control is coupled to the thumb grip extension portion on a second side of the thumb grip extension portion that is opposite to a first side of the thumb grip extension portion that includes a thumb grip surface. In some implementations, the thumb grip member includes a presence sensor configured to detect disengagement of the thumb from the thumb grip member, where the finger grip member includes a thumb input control configured to be activated by the thumb, and the thumb input control outputs signals that are configured to control one or more functions of the master control system in response to the presence sensor detecting the disengagement of the thumb from the thumb from the thumb grip member. In further implementations, the thumb grip member includes a presence sensor configured to detect disengagement of the thumb from the thumb grip member, and detection of the disengagement causes output of a control signal to the control device to cause the system to cease the master-slave control relationship.

In some implementations, a method of operating a teleoperated system includes establishing a master-slave control relationship between a master device and a slave instrument, where the master device includes a thumb grip member including a thumb grip receptive to a thumb of a hand of a user. The master device further includes a finger grip member coupled to the thumb grip member at a proximal end of the master device and extending toward a distal end of the master device, where the finger grip member includes a finger grip receptive to multiple fingers of the hand of the user, and where the thumb grip member and the finger grip member are movable within a pinching configuration with respect to each other. The method further includes sensing relative positions of the thumb grip member and the finger grip member with respect to each other in the pinching configuration. The method further includes determining a plurality of manipulations of one or more input controls of the hand controller. The method further includes providing control signals to the slave instrument based on the manipulations during the master-slave control relationship.

Various implementations and examples of the method are described. For example, in some implementations, the finger grip member includes a finger grip extension portion that is coupled to and extends from the finger grip member, and an input control provided on a surface of the finger grip extension portion, where the method further comprises sensing activation of the input control by a finger of the hand, and in response to sensing the activation of the input control, outputting an input control signal to the slave instrument. In some implementations, the thumb grip member includes a thumb grip extension portion that is coupled to the thumb grip member and extends from the thumb grip member in a direction away from the finger grip member, and an input control coupled to the thumb grip extension portion on a second side of the thumb grip extension portion that is opposite to a first side of the thumb grip extension portion that includes a thumb grip surface, where the method further includes sensing activation of the input control by the hand, and in response to sensing the activation of the input control, outputting an input control signal to the slave instrument.

DETAILED DESCRIPTION

Figure 1:
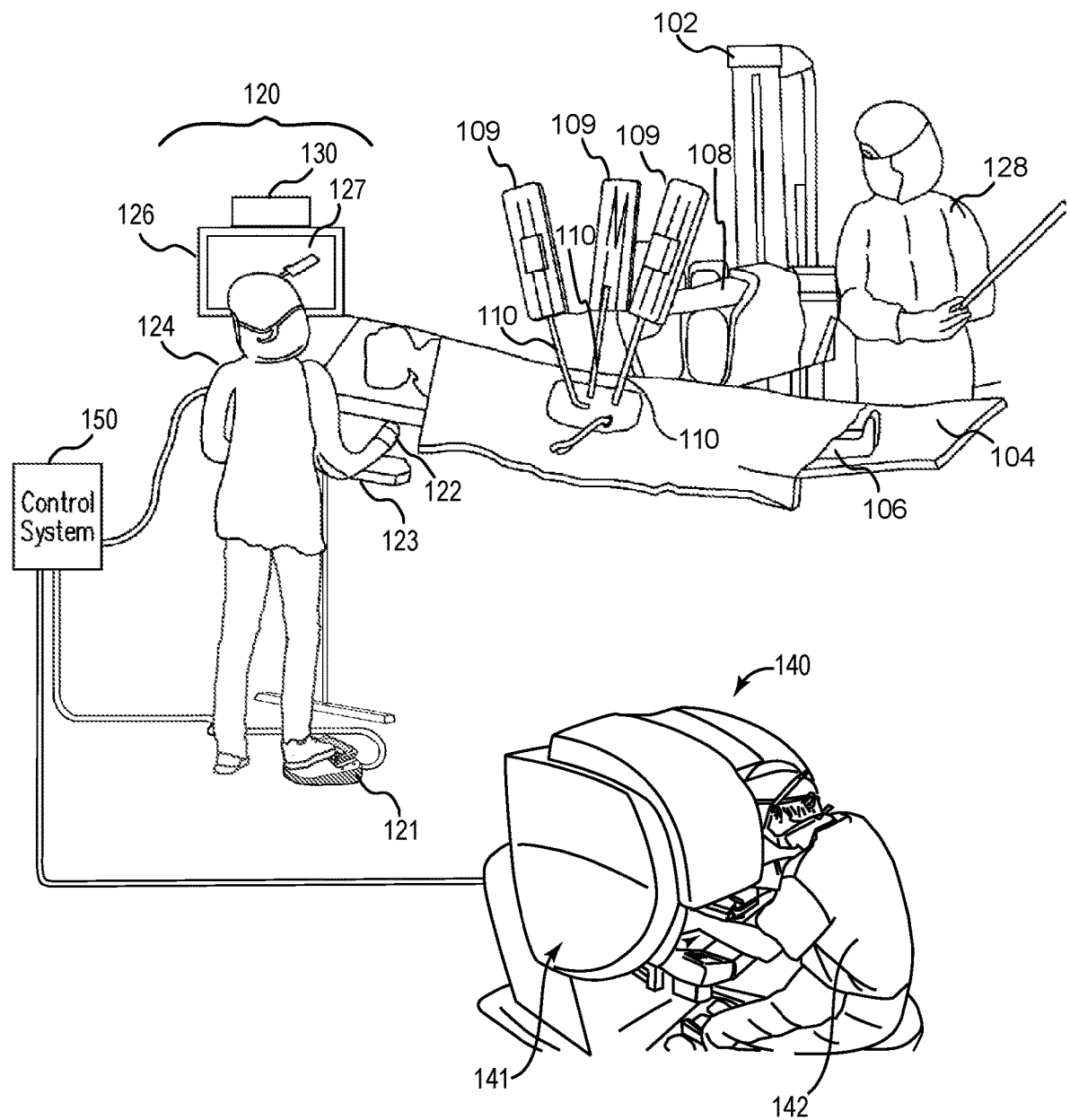
FIG. 1 is a diagrammatic view of an example teleoperated surgical system including a one or more master control devices, according to some implementations.

Implementations relate to a master control device, e.g., a master controller. As described in more detail herein, implementations provide a master controller enabling user control over multiple functions of a system, such as a teleoperated surgical system. The master controller is adapted to mechanically ungrounded operation by a user in a standing or sitting position, e.g., close to a patient or other site of operation. In some implementations, the master controller may be used in mechanically grounded operation. Functions activated at the activation positions can include functions of instruments used in teleoperated systems, e.g., surgical tools and other instruments used in treating patients, or other instruments in other types of procedures.

Described features of the master controller include a thumb grip member including a thumb grip receptive to a thumb of a hand of a user. The master controller also includes a finger grip member coupled to the thumb grip member at a proximal end of the master controller, where the grip members are movable in a pinching configuration with respect to each other. The finger grip member includes a finger grip receptive to multiple fingers of the hand of the user, e.g., placed adjacent to each other. A sensor coupled to at least one of the thumb grip member and the finger grip member is configured to sense relative positions of the grip members with respect to each other in the pinching configuration.

Various described features of the master controller include a finger grip extension portion that extends from the finger grip in a direction away from the thumb grip member, and/or a thumb grip extension portion that extends from the thumb grip in a direction away from the finger grip member. In some implementations, a central extension member can be coupled to the finger grip member and extend toward the thumb grip member, or can be coupled to the thumb grip member and extend toward the finger grip member. Input controls, e.g., buttons, switches, wheels, or other types of controls can be positioned on one or more of these extension portions and extension member. A sensor can be included to detect at least one of a position and an orientation of the master control device in a working environment of the master control device.

Described features provide various benefits. For example, a mechanically ungrounded hand controller described herein can be provided with control over operation and functions of a slave device, such as a surgical slave device. Users such as surgeons or other operators may use master controllers over long periods of time during operating procedures. Mechanically grounded master controllers may be used in such procedures with reduced fatigue because the grounded connection supports the weight of the controller via gravity compensation. Ungrounded master controllers, however, do not have this grounded connection, and thus an operator may become more fatigued in use of the controller over the duration of a surgical procedure. Furthermore, some ungrounded master controllers may have tethered connections (cables, etc.) that obstruct the movement of or add weight to the controller. In addition, ungrounded master controllers (or their tethered connections) may sometimes be knocked or otherwise impacted by the operator's other hand, another person, etc. These factors may cause an ungrounded master controller to slip in the hand of the user or drop out of the hand, which may cause inadvertent and dangerous movements of a controlled slave device. Furthermore, some mechanically grounded master controllers may have similar or other issues with slippage out of an operating hand, e.g., due to blocking structures within the working environment, unexpected collisions with objects, forces applied to the master controller, etc.

Features described herein provide accurate, secure, and safe manipulation of system functions using a master controller. Features such as a finger grip member that is configured to receive multiple fingers of the user's hand can provide additional stability and reduce fatigue when the controller is held due to multiple fingers contacting the controller and due to the natural positioning of the fingers next to each other, reducing strain. In some examples, the secure grip provided by the multi-finger grip can allow some constraining devices such as finger bands or loops to be avoided, thus increasing freedom of controller motion. Additional features such as a finger grip extension portion and/or a thumb grip extension portion are positioned to cradle the thumb and/or other fingers of the hand and offer additional security for holding the controller. For example, these extension portions can at least partially wrap over the thumb and/or other fingers, allowing the controller, if slipped or dropped, to be caught and supported by large portions of the fingers. Furthermore, extension portions and extension members allow a finger (e.g., the index finger) to contact the surface of the extension portion or member, securing the grip. In some cases, the finger can grip an extension portion or member against the thumb or against the other fingers to grasp the hand controller more securely, e.g., by squeezing the surface of the extension portion between the index finger and the thumb or third finger.

Additional features include input controls that are provided on extension portions of the master controller that enable the user to actuate the input controls to activate associated functions of a connected system. For example, an input control positioned on a described extension portion enables an activating finger, e.g., the index finger, to actuate the input control easily and accurately. Furthermore, the described positioning of the input controls enables the user's fingers to access the input controls while using the hand's fingertips to contact and manipulate the controller in space, e.g., allowing a fingertip range of motion of the controller. Such fingertip control provides accurate and wide-ranging manipulation of the controller, e.g., including preserving a large range of motion beyond the range of motion of the user's wrist. A rounded or curved proximal end of the controller allows the proximal end to be easily moved out of the palm, increasing fingertip control, or allows the proximal end to be pulled into contact with the palm for additional security.

These features provide additional accuracy and security, and reduce fatigue, in the operation of the hand controller, thus increasing accuracy of control and reducing incidences of inadvertent slippage or dropping of the hand controller by the user during controller operation. For example, due to the fatigue that surgeons or other operators may experience over an extended operation using ungrounded master controllers, the described controller features are useful in performing teleoperated surgical procedures and other procedures or tasks. The described features increase grasping security, reduce fatigue, and increase accuracy of control of the controller and are of high importance in procedures where accuracy and consistency in instrument control are required, e.g., medical procedures in which controlled surgical instruments operate on a live patient.

Various terms including "linear," "center," "parallel," "perpendicular," "aligned," or particular measurements or other units as used herein can be approximate, need not be exact, and can include typical engineering tolerances.

Some implementations herein may relate to various instruments and portions of instruments in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As used herein, a mechanically ungrounded master control device refers to a master controller that is unconstrained with respect to possible position and orientation motion in a large working environment (e.g., an operating area or room). Also, such a master controller is kinematically separated from the ground (e.g., not mechanically supported by a console, supports, or other object attached to the ground). In some implementations, a mechanically ungrounded master control device may be in tethered or untethered connection with one or more associated components such as control processors, data sources, sensors, power supplies, etc. For example, the master control device may be tethered, e.g., connected physically to these components via a cable or wire, or untethered, e.g., not physically connected to such components and in communication with the components via wireless communication signals.

Aspects of this invention augment the control capability of a computer-assisted teleoperated system through the use of one or more master controllers (e.g., one, two, three, or more) for providing instrument control in various procedures (surgical, procedures in extreme environments, or other procedures), instruction, supervision, proctoring, and other feedback to a user of the system. In some example implementations, master controllers may provide control of one or more of the operational surgical tools in the surgical environment or proxy surgical tools in a virtual environment. One example of a medical device system that may incorporate one or more of these master controllers (e.g., mechanically ungrounded or mechanically grounded) is the da Vinci® minimally invasive teleoperated medical system commercialized by Intuitive Surgical, Inc. of Sunnyvale, California.

Figure 11:
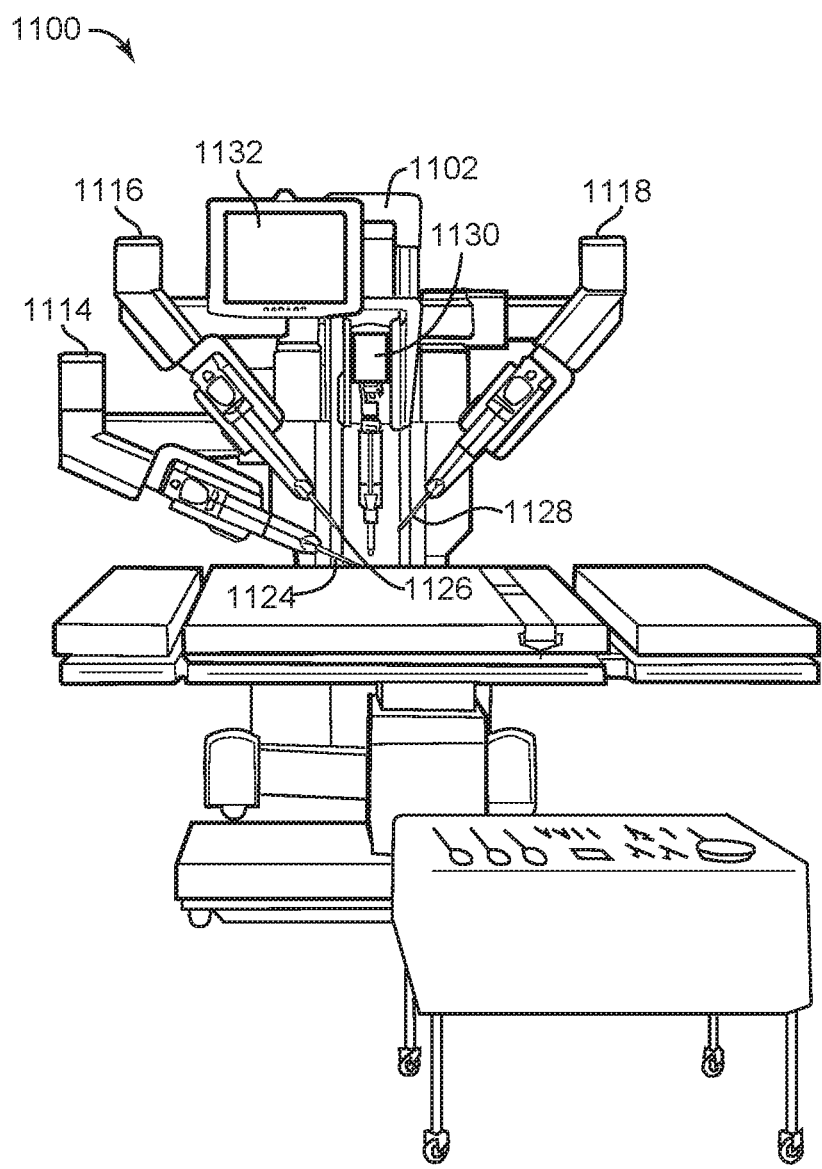
FIG. 11 is a diagrammatic illustration of an example teleoperated slave device and patient site, according to some implementations.

FIG. 1 is a diagrammatic view of an example teleoperated surgical system 100, including one or more master control devices, according to some implementations. As shown, the teleoperated surgical system 100 generally includes a teleoperated slave device 102 mounted to or near an operating table 104 (e.g., table, bed, or other support) on which a patient 106 is positioned. The teleoperated slave device 102 includes a plurality of manipulator arms 108, each coupled to an instrument assembly 109. An instrument assembly 109 may include, for example, instruments 110. In some examples, instruments 110 may include surgical instruments or surgical tools. In some implementations, a surgical instrument can include a surgical end effector at its distal end, e.g., for treating tissue of the patient. In various implementations, surgical instruments can include cameras, e.g., cameras for use with surgical procedures. Some examples of an arm assembly for the teleoperated slave device 102 are shown in FIG. 11.

The teleoperated surgical system 100 includes an ungrounded master controller system 120. In this example, master controller system 120 includes one or more mechanically ungrounded master control devices 122 ("master controllers"), some implementations of which are described below, for use by a user 124. The master control device 122 includes at least one mechanically ungrounded, unpowered master tool, e.g., hand controller, contacted or grasped by hand of the user 124. In some implementations, two or more mechanically ungrounded unpowered master tools can be used, e.g., one tool used by each hand of user 124. Example implementations of a master control device 122 are described in more detail below. The master control device 122 can be operated in a sterile surgical field close to a patient, as described below. An ergonomic support 123 (e.g., forearm rest) may be provided in the sterile surgical field to support the user's forearms or elbows as the user 124 manipulates master control device 122, e.g., during a surgical procedure.

In some implementations, the slave manipulator arms 108 and/or instrument systems 109 may be controlled to move and articulate the instruments 110 in response to manipulation of master control device 122 by the user 124, so that the user 124 can direct surgical procedures at internal surgical sites through minimally invasive surgical apertures. For example, one or more actuators coupled to the manipulator arms 108 and/or instrument systems 109 may output force to cause links or other portions of the arms 108 and/or instruments 110 to move in particular degrees of freedom in response to control signals received from the master control device 122.

The number of teleoperated surgical instruments 110 used at one time, and/or the number of arms 108 used in slave device 102, may depend on the medical procedure to be performed and the space constraints within the operating room, among other factors. If it is necessary to change one or more of the surgical instruments being used during a procedure, an assistant 128 may remove a surgical instrument no longer being used from its arm 108 or instrument assembly 109 and replace that surgical instrument with another surgical instrument from a tray in the operating room.

Some implementations of the teleoperated surgical system 100 can provide different modes of operation. In some examples, in a non-controlling mode (e.g., safe mode) of the teleoperated surgical system 100, the controlled motion of the teleoperated slave device 102 is disconnected from the master control device 122 in disconnected configuration, such that movement and other manipulation of the master control device 122 does not cause motion of the teleoperated slave device 102. In a controlling mode of the teleoperated system 100 (e.g., following mode), motion of the teleoperated slave device 102 can be controlled by the master control device 122 such that movement and other manipulation of the master control device 122 causes motion of the teleoperated slave device 102, e.g., during a surgical procedure. Some examples of such modes are described in greater detail below.

In this example, user 124 may be a surgeon controlling the movement of instrument systems 108 or a proctor providing supervision and/or instruction for a different surgeon or user (e.g., proctor surgeon 142). Each manipulator arm 108 and the teleoperated instrument assembly 109 controlled by that manipulator may be controllably coupled to and decoupled from mechanically ungrounded master control devices 122. For example, user 124 may sit or stand at the side of patient 106 while working in a sterile surgical field and view display device 126 during a surgical procedure. User 124 performs a medical procedure by manipulating at least master control device 122. In some examples, user 124 grasps master control device 122 in configurations described herein so that targeting and grasping involve intuitive pointing and pinching motions. As the user 124 moves master control device 122, sensed spatial information and sensed orientation information is provided to control system 110 based on the movement of master control device 122.

In some implementations, a hand-tracking transceiver 130 can be included in the ungrounded master controller system 120. For example, hand-tracking transceiver 130 can be positioned to generate a field, for example an electromagnetic field, an optical field (e.g., light beams), etc., in proximity to the user 124. The movement of master control device 122 in this field provides sensed spatial position and orientation information in a three-dimensional coordinate system, e.g., sensed by the transceiver 130 and/or other sensors (e.g., sensors positioned at other locations of the working volume). In some examples, the transceiver 130 can be or include an electromagnetic spatial tracking system, an inertial spatial tracking system, an optical spatial tracking system, a sonic spatial tracking system, etc. The device that senses and outputs sensed information may vary depending on the particular spatial tracking system or combination of tracking systems used. In each implementation, at least sensed position and orientation information for a master control device 122 are provided to a control system 150.

In some implementations, the ungrounded master controller system 120 also includes a display device 126. In some implementations, images captured by one or more cameras of the teleoperated slave device 102 (e.g., on an instrument assembly 109) can be transmitted to the display device 126 and/or transmitted to one or more other displays, e.g., a display coupled to the teleoperated slave device 102 (not shown), a display of the operator input system 120, etc. For example, a surgical environment near or within the patient 106 and the real or virtual instruments controlled by the ungrounded master control device 122 can be displayed by the display device 126 and viewed by the user 124 while the user is operating the ungrounded master controller system 120. Display device 126 can provide a two dimensional image 127 and/or a three-dimensional image 127 of, for example, an end effector of a slave surgical instrument 110 and the surgical site. In some examples, display device 126 provides an output that the user perceives as a three-dimensional image that includes an image 127 of an end effector of a slave surgical instrument 110 and the surgical site. The end effector is located within a sterile surgical field. The three-dimensional image provides three-dimensional depth cues to permit user 124 to assess relative depths of instruments and patient anatomy. The three-dimensional depth cues permit user 124 to use visual feedback to steer the end effector of slave surgical instrument 110 using master control device 122 and/or an optional foot controller 121 to precisely target and control features.

Various embodiments of an ungrounded master control device are disclosed in U.S. Pat. No. 8,521,331 B2 (issued on Aug. 27, 2013, titled "Patient-side Surgeon Interface For a Minimally Invasive, Teleoperated Surgical Instrument"), which is incorporated herein by reference in its entirety.

In some implementations, ungrounded master controller system 120 has at least one component within a sterile surgical field of the surgery. The sterile surgical field is a non-contaminant zone or space near the surgical site in which contaminants are reduced to reduce potential bacterial (or other) contamination to the surgical site during surgery. During surgery, the distal end of at least one teleoperated surgical instrument 110 is positioned within a sterile surgical field. In some implementations, the one or more components in the sterile field can include the master control device(s) 122. For example, master control device 122 is either sterile or draped so that master control device 122 may be safely positioned and used within a sterile surgical field for the surgery. This feature in combination with an image on display device 126 allows a user 124 to control teleoperated slave surgical instruments 110 from within the sterile surgical field. Thus, ungrounded master controller system 120 permits a user 124 to work within the sterile surgical field adjacent a patient 106 undergoing surgery.

Controlling minimally invasive slave surgical instruments 110 from within the sterile surgical field permits minimally invasive surgery combined with direct visualization of patient 106, teleoperated slave device 102, any manually operated surgical instruments, other machines and/or instruments being used in the surgery, etc., by user 124. In some examples, the proximity to patient 106 allows user 124 to control an end effector of teleoperated slave surgical instrument 110 together with one or more manually controlled instruments, such as a laparoscopic instrument or a stapler.

Ungrounded master controller system 120 can reduce operating room floor requirements for the teleoperated surgical system 100. Ungrounded master controller system 120 may provide a lower-cost alternative to a grounded input system 140 (e.g., surgeon's console 141) in a conventional minimally invasive, teleoperated surgical system. For example, ungrounded master controller system 120 can improve safety by allowing user 124, who is performing the operation, to directly observe patient 106 and teleoperated slave device 102 while manipulating instruments 110. System 120 also allows the single user 124 to operate in the sterile surgical field and perform procedures which require coordinated use of manual surgical instruments and one or more teleoperated slave surgical instruments. System 120 promotes collaborative procedures without requiring additional large stand-alone surgeon consoles. In some implementations, assistant 128 may share system 120 to operate other surgical instruments. In addition, multiple users (e.g., surgeons or clinicians 124, 128, 142, etc.) may collaborate using a common display device 126.

In some implementations, the teleoperated surgical system 100 may also include a grounded input system 140, which allows a second user 142 (e.g., a surgeon, proctor surgeon, or other type of clinician) to view images of or representing the work site and to control the operation of the manipulator arms 108 and/or the instrument assemblies 109. In some implementations, the grounded input system 140 may be located at a console 141, e.g., a surgeon console, which can be located in the same room as operating table 104. In various implementations, the user 142 can be located in a different room or a completely different building from the patient 106. For example, the surgeon console 141 can be located outside the sterile surgical field.

In this example teleoperated system 100, grounded input system 140 includes one or more mechanically grounded master control device(s) ("master controllers") for controlling the manipulator arms 108 and the instrument assemblies 109. The grounded master controllers may include one or more of any number of a variety of coupled input devices, such as kinematically linked (mechanically grounded) hand grips, joysticks, trackballs, data gloves, trigger-guns, hand-operated controllers, voice recognition devices, touch screens, body motion or presence sensors, and the like. In some implementations, the grounded master controllers are provided with the same degrees of freedom as the slave instruments of the teleoperated assembly to provide the operator with telepresence, the perception that the master controllers are integral with the instruments so that the operator has a strong sense of directly controlling instruments as if present at the work site. In other implementations, the master controllers may have more or fewer degrees of freedom than the associated instruments and still provide the operator with telepresence. In some implementations, the master controllers are manual input devices which move in all six Cartesian degrees of freedom, and which may also include an actuatable handle for actuating instruments (for example, for closing grasping jaws, applying an electrical potential to an electrode, delivering a medicinal treatment, and the like). Such a grip function is an additional mechanical degree of freedom (i.e., a grip DOF). In some examples, each manipulator arm 108 and the teleoperated instrument system controlled by that manipulator arm may be controllably coupled to and decoupled from the master controllers of input system 140. In some implementations, the grounded master controllers of the input system 140 can include one or more features of hand controllers as described in implementations herein.

The teleoperated surgical system 100 also includes a control system 150. The control system 150 includes at least one memory and at least one processor (not shown), and typically a plurality of processors, for effecting control between the teleoperated slave device 102, the ungrounded master control system 120, and the grounded input system 140. The control system 150 also includes programmed instructions (e.g., a computer-readable medium storing the instructions) to implement some or all of the appropriate operations and blocks of methods in accordance with aspects disclosed herein.

For example, control system 150 maps sensed spatial motion data and sensed orientation data describing the master control device 122 in space to a common reference frame. Control system 150 may process the mapped data and generate commands to appropriately position an instrument 110, e.g., an end effector or tip, of teleoperated slave device 102 based on the movement (e.g., change of position and/or orientation) of master control device 122. Control system 150 can use a teleoperation servo control system to translate and to transfer the sensed motion of master control device 122 to an associated arm 108 of the teleoperated slave device 102 through control commands so that user 124 can manipulate the instruments 110 of the teleoperated slave device 102. Control system 150 can similarly generate commands based on activation or manipulation of input controls of the master control device 122 to perform other functions of the slave device 102 and or instruments 110, e.g., move jaws of an instrument end effector, activate a cutting tool or output energy, activate a suction or irrigation function, etc.

While control system 150 is shown as a single block in FIG. 1, the system may include two or more data processing circuits with one portion of the processing optionally being performed on or adjacent the teleoperated slave device 102, another portion of the processing being performed at the ungrounded master controller system 120, another portion of the processing being performed at the grounded input system 140, etc. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 110 supports one or more wireless communication protocols such as Bluetooth, IrDA, HomeRF, IEEE 802.11, DECT, and Wireless Telemetry.

In some implementations, user 124, from within the sterile surgical field, can control at least one proxy visual to a proctor surgeon 142 at the surgeon's console 141. For example, the proxy visual is visible both in display device 126 and in a display device viewed in surgeon's console 141. Using master control device 122, user 124 can manipulate the proxy visual of a surgical instrument to demonstrate control and use of teleoperated slave surgical instruments 110 while second user (e.g., proctor surgeon) 142 uses master controllers of the surgeon's console 141 to control a teleoperated slave instrument 110. Alternatively, second user 142 can control the proxy visual, using a master controller on the surgeon console 141, to instruct user 124. In some implementations, user 124 can telestrate (e.g., draw a freehand sketch over a moving or still video image), or can control a virtual hand or other pointer in the display. In some implementations, user 124 can demonstrate how to manipulate a master tool grip on the surgeon's console 140 by manipulating a virtual image of master tool grip that is presented in the display device 126 and on surgeon console 140. To facilitate proctoring, a proxy visual module (not shown) of the controller 110 can be processed as part of a vision processing subsystem. For example, the executing module receives position and orientation information, input control states (e.g., switch states, variable slider state, etc.), presence states, grip state, or other information from the master controller 122 and renders stereo images, which are composited with the endoscopic camera images in real time and displayed on any combination of surgeon's console 141, display device 126, or any other display systems in the surgical environment.

In some implementations, a controlled teleoperated slave device 102 can be a virtual representation of a device, e.g., presented in a graphical training simulation provided by a computing device coupled to the teleoperated surgical system 100. For example, a user can manipulate master hand controller devices to control a displayed representation of an end effector in virtual space of the simulation, similarly as if the end effector were a physical object coupled to a physical slave device. Some implementations can use master hand controller devices in training, e.g., demonstrate the use of instruments and controls of a workstation including controller devices.

In some implementations, non-teleoperated systems can also use one or more features of the master control devices as described herein. For example, various types of control systems and devices, peripherals, etc. can be used with described master controllers.

Some implementations can include one or more components of a teleoperated medical system such as a da Vinci® Surgical System (e.g., a Model IS3000 or IS4000, marketed as the da Vinci® Si® or da Vinci® Xi® Surgical System), commercialized by Intuitive Surgical, Inc. of Sunnyvale, California Features disclosed herein may be implemented in various ways, including teleoperated and, if applicable, non-teleoperated (e.g., locally-controlled) implementations. Implementations on da Vinci® Surgical Systems are merely examples and are not to be considered as limiting the scope of the features disclosed herein. For example, different types of teleoperated systems having slave devices at worksites can make use of actuated controlled features described herein.

Figure 2:
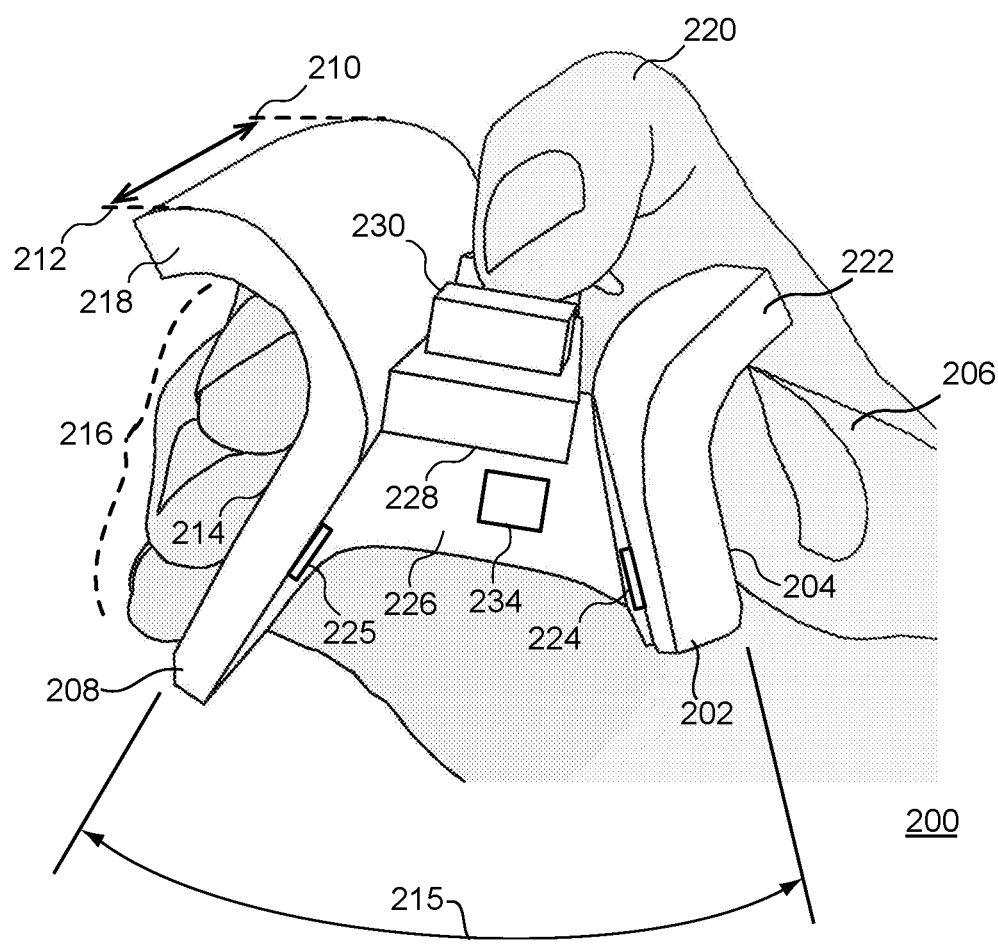
FIG. 2 is a perspective view of an example of a master controller being manipulated by a user's hand, according to some implementations.

FIG. 2 is a perspective view of an example of a surgical system master control device 200, e.g., master controller or hand controller 200, being manipulated by a user's hand, according to some implementations. In some examples, hand controller 200 can be an ungrounded master controller configured to be held by a user's hands and that is mechanically ungrounded during its operation. For example, the hand controller 200 can be used as a master control device 122 as described with reference to FIG. 1, or in other master control applications. The hand controller 200 is contacted and held by a user to provide control signals to one or more systems in communication with the hand controller. FIG. 2 shows a front view of the hand controller 200, while FIG. 3 (described below) shows a side view of the hand controller 200.

Herein, the fingers of the user's hand are referred to as the thumb for a first finger, the second finger for the index finger or forefinger, the third finger for the middle finger, the fourth finger for the ring finger, and the fifth finger for the pinky finger.

As shown, in this example implementation, the hand controller 200 includes a thumb grip member 202 including a thumb grip (e.g., including a thumb grip surface) 204 receptive to a thumb 206 of a hand of a user. The thumb grip member 202 can extend from a proximal end 210 of hand controller 200 (more clearly shown in FIG. 3) toward a distal end 212 of hand controller 200. Hand controller 200 also includes a finger grip member 208 coupled to the thumb grip member 202 at the proximal end 210 of hand controller 200, where the finger grip member 208 extends toward the distal end 212 of hand controller 200. In some implementations, finger grip member 208 includes a finger grip (e.g., including a finger grip surface) 214 receptive to and engaging multiple fingers 216 (non-thumb fingers) of the hand of the user. In this example, the finger grip 214 engages the third (middle) finger, fourth (ring) finger, and fifth (pinky) finger of the hand of the user. In some implementations, the thumb grip member 202 and the finger grip member 208 are movable in a pinching configuration with respect to each other, as described below.

In some implementations, the thumb grip member 202 and the finger grip member 208 extend at a particular neutral position angle relative to each other when in a neutral position (e.g., without force being applied to the grip members by a user). The angle between grip members changes as the grip members 202 and 208 open and close, e.g., are pinched closer to each other and move away from each other. For example, the neutral position angle may vary depending on the particular implementation, 30 degrees, 60 degrees, etc. In some implementations, thumb grip member 202 and the finger grip member 208 can extend approximately parallel to each other from the proximal end 210 to the distal end 212 of the hand controller 200, e.g., parallel to a central axis 304 (see FIG. 3) of the hand controller 200. The thumb grip member 202 and the finger grip member 208 may also extend at a particular grip angle 215 relative to each other in the neutral position, e.g., in a dimension approximately perpendicular to the central axis 304. For example, the grip angle 215 can be 40 degrees, 60 degrees, 90 degrees, etc.

Each of the thumb grip 204 and the finger grip 214 is positioned to contact one or more of the user's fingers. In some implementations, each grip 204 and 214 can have a surface that is shaped to receive a finger (e.g., finger pad) of the user. In various example implementations, the grips 204 and 214 have a contact surface that is flat (e.g., parallel to the respective thumb grip members 202 and finger grip member 208), concave (curved inward to form a valley to fit the finger), or convex (curved outward to form a bump or shell engaged by the finger) to provide engagement and secure contact with the fingers of the operating hand. The grips 204 and 214 can have a tapered surface in some examples. Some implementations can provide protrusions that extend outwardly from the grips 204 and 214 in which to cradle a finger, or an aperture in which a finger is inserted. Some implementations of the grips 204 and 214 can include texturing such as bumps, ridges, or other patterns of features (some examples are described below) to engage the user's finger(s).

In various implementations, the finger grip member 208 is configured and sized to receive multiple fingers positioned adjacent to each other. For example, as shown, the finger grip member 208 can be a multiple-finger grip, where the finger grip member 208 has a grip 214 (e.g., grip surface) that is of sufficient width to allow the multiple fingers to engage the surface of the single finger grip 214 at their finger pads or finger tips when positioned adjacent to each other. In the example shown, the third, fourth, and fifth fingers of the hand are positioned adjacent to each other and the finger pads of these fingers are engaged with the finger grip 214. In other implementations, a narrower finger grip 214 can be used and two adjacent fingers can be engaged by the finger grip 214 (e.g., the third and fourth fingers, or the fourth and fifth fingers). In some implementations, the finger grip 214 can be larger such that four adjacent fingers can be engaged by the finger grip 214.

In some implementations, the finger grip 214 can include adjacent physical features that can guide and/or provide additional contact to the fingers engaged with the finger grip 214. In some examples, the physical features can include concave depressions on the surface of finger grip 214 to engage multiple fingers side-by-side, e.g., the third and fourth fingers, the fourth and fifth fingers, or the third, fourth, and fifth fingers (e.g., with the thumb grip 204 engaging the first finger, e.g., thumb). In another example, the finger grip 214 can include protrusions that extend outwardly from the grip 214 to form areas in which to cradle the multiple fingers adjacent to each other. In one such example, the protrusions can be about the height of a finger and spaced apart about the width of a finger, allowing multiple fingers to be cradled in adjacent spaces between the protrusions.

In some implementations, the finger grip member 208 may include a finger grip extension portion 218 that extends from the finger grip 214, e.g., in a direction at least partially away from the thumb grip member 202. For example, the finger grip extension portion 218 can be positioned between the multiple fingers 216 and one or more other fingers, e.g., the second (index) finger 220 and thumb 206 of the hand. For example, the finger grip extension portion 218 can extend approximately perpendicularly from the surface of the finger grip 214 away from the thumb grip member 202.

In some implementations, as shown in FIG. 2, the finger grip extension portion 218 can extend from the finger grip 214 toward and past the multiple fingers 216 that engage the finger grip 214 so that the extension portion 218 extends at least partially over the multiple fingers 216, e.g., with respect to the controller 200 orientation as shown in FIG. 2. In some examples, the finger grip extension portion 218 curls or wraps at least partially around and over the fingers 216 from one side or edge of the finger grip 214 (e.g., the top side in the orientation of FIG. 2). In some implementations, the extension portion 218 can curl greater than 90 degrees relative to the surface of finger grip 214, e.g., around the space occupied by the third finger of the hand. In some examples, the extension portion 218 can curl much more than 90 degrees relative to surface of finger grip 214, e.g., almost 180 degrees.

In some implementations or usages, at least one of the fingers 216 is contacted by the finger grip extension portion 218 during controller operation. In some implementations or usages, the fingers 216 are not contacted in this way during operation, thus allowing greater range of motion to the fingers 216 and allowing greater fingertip control of the controller 200. For example, the fingertips of fingers 216 can contact the finger grip 214 and the fingertip of the thumb 206 can contact the thumb grip 204 to manipulate the controller 200 with the fingertips, providing a large range of motion and orientation to the controller. The proximal end 210 of the controller can be made curved and/or sufficiently short in length to allow the proximal end to easily move out of and into the area near the palm of the hand, as well as easily move between the thumb and forefinger of the hand. When palm contact or security is desired during operation, the user can move the controller 200 toward the palm such that the proximal end 210 is near or contacting the palm.

One of the benefits of the finger grip extension portion 218 is that it can increase the security of the grip on the hand controller 200 for the hand. For example, the finger grip extension portion 218 can secure the grip on finger grip 214 by the multiple fingers 216, e.g., by preventing the finger grip 214 from sliding toward the bottom of FIG. 2 relative to the multiple fingers in the direction of gravity. In uses where the at least one of the fingers 216 contacts the finger grip extension portion 218, the extension portion prevents or reduces the ability of the hand controller 200 to slip down and out of the user's hand during use of hand the controller 200. In uses where the fingers 216 do not contact the finger grip extension portion 218 during operation, the presence of the extension portion provides security, e.g., if the controller 200 slips down, the extension portion 218 will be caught on the user's finger. In some implementations, the finger grip extension portion 218 allows the hand controller 200 to be supported, for operation or controller slips, by a portion of the length of the finger(s) that are cradled by the wrapped portion of the finger grip extension portion.

Furthermore, in some implementations, the shape of the portion 218 can allow the user to move the second and third fingers closer or further from each other for more or less security in holding the controller. In some examples, the second and third fingers can pinch the extension portion 218 between them for additional security, or the second finger can be moved away.

In addition, in some implementations, if the third finger is tucked underneath and/or cradled within the extension portion 218 while flexing the last joint or two last joints of the third finger, this finger is pushed against the sides of portion 218 within the cradled space and is held in place by friction against the surfaces of the portion 218, creating additional grasping security. Implementations in which extension portion 218 wraps around the third finger more than 90 degrees relative to the surface of finger grip 214 can provide greater security in this manner.

In some implementations, the finger grip extension portion 218 is configured to be contacted by, or be positioned adjacent to, the third, fourth, and/or fifth fingers of the hand on a first side (e.g., grip side) of the finger grip extension portion 218, e.g., where the first side is adjacent to the surface of finger grip 214 engaged by the multiple fingers. In such implementations, the finger grip extension portion 218 can also be contacted or accessed by a second finger (e.g., index finger or forefinger) 220 of the hand on a second side of the finger grip extension portion 218, e.g., the side opposite to the first side. For example, the second side of the finger grip extension portion 218 is close to a central lengthwise axis of the controller 200 (from proximal end to distal end) and can be within selective access of the second finger 220. In some examples, the second side of the finger grip extension portion 218 can support one or more input controls for access by the second finger 220, as described below. The input controls can be activated, e.g., by the second finger 220, to send input control signals to a control system in communication with the hand controller 220.

As shown, in some implementations, the thumb grip member 202 can include a thumb grip extension portion 222 that extends from the thumb grip member 202, e.g., in a direction a least partially away from the finger grip member 208. For example, thumb grip extension portion 222 can extend approximately perpendicularly from a surface of the thumb grip member 202 away from the finger grip member 208. In some implementations, as shown, the thumb grip extension portion 222 can extend at least partially over the thumb 206 engaged with the thumb grip 204, e.g., with respect to the controller 200 orientation as shown in FIG. 2. In some examples, the thumb grip extension portion 202 curls or wraps at least partially around and over the thumb 206 from one side or edge of the thumb grip 204 (e.g., the top side in the orientation of FIG. 2).

In some implementations or usages, thumb 206 is contacted by the thumb grip extension portion 222 during controller operation. In some implementations or usages, the thumb 206 is not contacted in this way during operation, thus allowing greater range of motion to the thumb 206 and allowing greater fingertip control of the controller 200 similarly as described above.

Similarly as described above for some implementations of the finger grip extension portion 218, one of the benefits of the thumb grip extension portion 222 is that it can increase the security of the grip on the hand controller 200 for the hand. For example, the thumb grip extension portion 222 can secure the thumb 202 to the thumb grip 204, e.g., by preventing the thumb grip 204 from sliding toward the bottom of FIG. 2 relative to the thumb in the direction of gravity. In uses where the thumb contacts the thumb grip extension portion 222, the extension portion prevents or reduces the ability of the hand controller 200 to slip down and out of the user's hand during use of hand the controller 200. In uses where the thumb does not contact the thumb grip extension portion 222 during operation, the presence of the extension portion provides security, e.g., if the controller 200 slips down, the extension portion 222 will be caught on the user's finger. In some implementations, the thumb grip extension portion 222 allows the hand controller 200 to be supported, for operation or controller slips, by a portion of the length of the thumb that is cradled by the wrapped portion of the thumb grip extension portion.

In some implementations, the thumb grip extension portion 222 can be configured to be contacted by, or be positioned adjacent to, the thumb 202 on a first side (e.g., grip side) of the thumb grip extension portion 222, e.g., where the first side is adjacent to the surface of thumb grip 204 engaged by the thumb. The thumb grip extension portion 222 can be configured to be contacted or accessed by a second finger 220 of the hand on a second side of the thumb grip extension portion 222, e.g., the side opposite to the first side. For example, the second side of the thumb grip extension portion 222 is close to the central lengthwise axis of the controller 220 and can be within selective access of the second finger 220. In some examples, the second side of the thumb grip extension portion 222 can support one or more input controls for access by the second finger 220, as described below. The input controls can be activated to send input control signals to a control system in communication with the hand controller 220.

As shown, the thumb grip member 202 and the finger grip member 208 are positioned opposite from each other, where the thumb grip member 202 and the finger grip member 208 can be grasped, held, or otherwise contacted by a user's fingers. In some implementations, the thumb grip member 202 and the finger grip member 208 are movable in a pinching motion or configuration with respect to each other. In some examples, the thumb grip member 202 and the finger grip member 208 may be pivotally or rotatably attached to each other at a pivoting end 226 of the hand controller 200, which is the proximal end 210 of the hand controller 200 in the example shown. For example, the thumb grip member 202 and the finger grip member 208 can be moved simultaneously in a pincher-type of movement, e.g., toward or away from each other. In some implementations, the thumb grip member 202 and finger grip member 208 are portions of a single unitary member, where the grip members 202 and 208 can pivot relative to each other at a flexible connection portion or hinge formed in the unitary member at the proximal end 210. In some implementations, the grip members 202 and 208 can be separate pieces that are rotatably coupled to each other with a rotary coupling.

In various implementations, the hand controller 200 includes one or more grip sensors configured to sense relative positions of the thumb grip member 202 and the finger grip member 208 with respect to each other in the pinching configuration. In some examples, a grip sensor can be coupled to one or more of the thumb grip member 202 and the finger grip member 208. In the example of FIG. 2, a grip sensor 224 is coupled to the thumb grip member 202. A corresponding sensed element 225 is positioned on the finger grip member 208, such that the grip sensor 224 can detect the presence and/or distance between the sensor 224 and the sensed element 225 as the thumb grip member 202 and the finger grip member 208 are moved toward and away from each other by the user's hand, e.g., in a pinching motion or configuration. In other implementations, the grip sensor 224 and sensing element 225 can be in positions opposite to those shown in FIG. 2, or at different locations on the grip members 202 and 208 (e.g., closer to the proximal end 210, closer to the top of the grip members 202 and 208 in the orientation of FIG. 2, etc.). In some examples, the grip sensor 224 can be a Hall effect sensor or other type of sensor and the sensing element 225 can be a magnet or include magnetic material. In other examples, the grip sensor can be an optical sensor, rotary or linear potentiometers or encoders, inductive or eddy current sensor, a strain gage, etc.

In some implementations, each of the grip members 202 and 208 can be provided with a respective degree of freedom in which the grip member is moved. For example, each grip member 202 and 208 can be moved relative to a central member to which each grip member is rotatably or pivotally coupled. In such implementations, one or more grip sensors coupled to the hand controller 200 can detect the positions of the grip members 202 and 208 in their degrees of freedom. For example, optical encoders, potentiometers, or other sensors can be used for the grip sensors.

The grip sensor 224 (or other grip sensors) can output sensor signals describing the relative positions of the thumb grip member 202 and the finger grip member 208, and/or can output signals describing the positions of these grip members 202 and 208 in their degrees of freedom. The sensor signals can be output to one or more control circuits of the system to which the hand controller 200 is connected, e.g., teleoperated surgical system 100 or other system. In some examples, the control circuits provide control signals to the teleoperated slave device 102, examples of which are described with reference to FIGS. 1, 11 and 12. For example, the positions of the grip members 202 and 208 relative to each other or in their degrees of freedom can be used to control components of slave instruments such as jaws or other components, or any of various degrees of freedom of an end effector of a controlled slave device (e.g., teleoperated slave device 102). In some examples, the two grips members 202 and 208 of the hand controller 200 can be moved together or apart by the user in pincher motions to, for example, correspondingly move forceps, pliers, or other instrument end effectors of the teleoperated slave device.

In some implementations, one or more springs or other actuators (not shown) can be provided between the grip members 202 and 208, to provide a resistive force in particular directions of movement of the grip members 202 and 208 (e.g., movement in directions toward each other). In some implementations, after the grip members 202 and 208 have been moved toward each other by the user from a fully open position (neutral position) (e.g., as shown in FIG. 2), springs or actuators can provide a restoring force to the grip members 202 and 208 toward the neutral position of the grip members 202 and 208. When the user reduces sufficient closing force on the grip members 202 and 208 provided by the fingers, the grip members 202 and 208 may be moved toward the neutral position by the restoring force.

In various implementations, resistance and/or restoring force on the grip members can be provided by various types of actuators, e.g., passive actuators that provide a passive resistive force to movement (such as springs that provide an increasing resistive force the closer the grip member is moved to the central portion, or, dampers, resistive elements, etc.) and/or active actuators (motors, voice coils, etc.) that provide an active force. In some implementations, the actuator(s) can provide forces that are varied based on a control signal provided to the actuator(s) from a controller. In some examples, the grip members 202 and 208 can include a power assist mechanism using one or more actuators to provide assistive force to the grip members and assist the user when moving a grip member between positions. In some implementations, other types of forces can be provided (e.g., damping force, force pulses or vibrations, etc.). In some examples, a sensor and/or actuator can be housed in the hand controller 200, which is coupled to the grip members 202 and 208 by a transmission.

In various implementations, the hand controller 200 may include a central extension member 228 extending, for example, from the finger grip member 208 toward the thumb grip member 202. As shown, in some implementations, the central extension member 228 can be attached to the finger grip member 208. In some implementations, the central extension member 228 can alternatively be attached to the thumb grip member 202. In some implementations, a gap 229 can be provided between the central extension member 228 and the grip member that is not attached to the central extension member (e.g., thumb grip member 202 in FIG. 2) to allow the grip members 202 and 208 to move together. In some examples, the central extension member 228 can support one or more input controls for access by the second finger 220, as described below.

In various implementations, the hand controller 200 can include an input control 230 provided on a surface of the central extension member 228 between the finger grip member 208 and the thumb grip member 202. For example, the input control 230 can be provided on a top surface of the central extension member 228, with respect to the orientation shown in FIG. 2. In various implementations, the input control 230 can include one or more sensors (e.g., mechanical switches or buttons, optical sensors, magnetic sensors, capacitive sensors, pressure sensors, etc.) that detect user input, e.g., the engagement or activation of a user's finger with the input control. The various sensors of the input control 230 can be used to detect activations of control signals by the user by, e.g., detecting a position of a finger or a threshold amount of contact with a finger of the user's hand. The input control 230 may also be referred to as an activation control, activation control switch, or activation control button.

Figure 3:
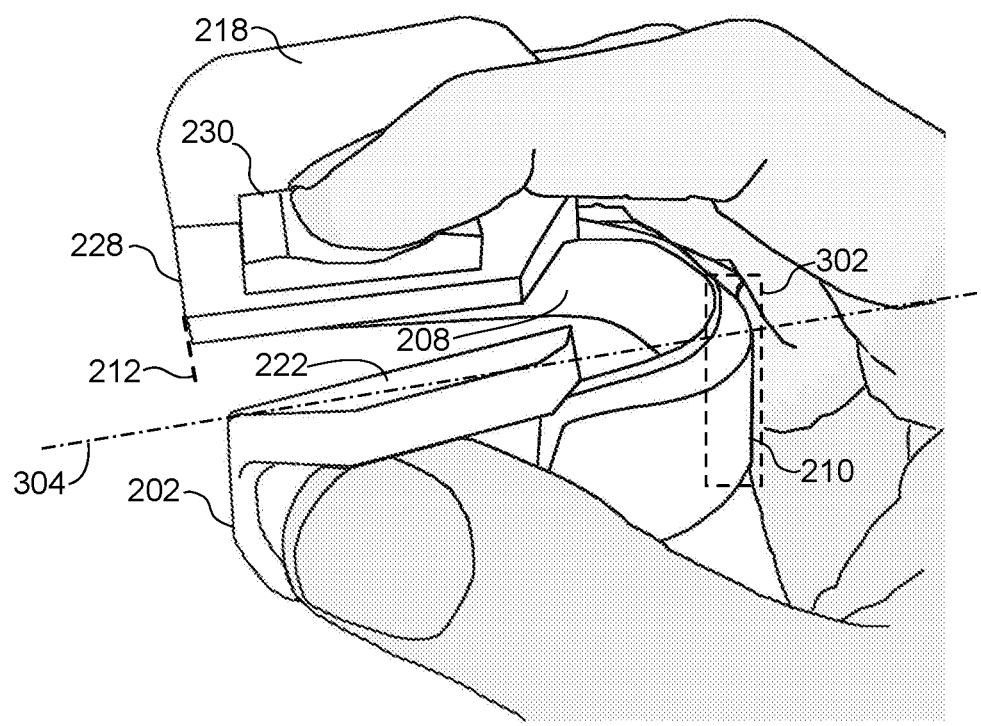
FIG. 3 is another perspective view of the master controller of FIG. 2 being manipulated by a user's hand, according to some implementations.

In various implementations, the input control 230 can be a sliding switch as shown, which can be moved forward or back (e.g., along the lengthwise axis of the controller as shown in FIG. 3). The input control 230 is configured to be activated by user input, e.g., engaged, slid, or pressed downward by at least a portion of a finger of the user that is operating the hand controller 200. In some implementations, the input control 230 can be a rocker, a wheel, a knob, a physical button, a joystick, a trackball, etc. Various other types of input controls can be also or alternatively be used to enable user activation of a control signal, e.g., optical sensor areas, capacitive sensor areas, pressure sensors, etc. Example implementations directed to a rocker control are described in more detail herein in connection with FIG. 4. Example implementations directed to a wheel are described in more detail herein in connection with FIG. 5.

The input control 230 can engage a user's finger during operation of the hand controller 200. For example, the input control 230 can be selectively accessed, engaged and activated by a second finger 220 located between fingers 206 and 216 on the user's hand that operate the finger grips 202 and 208. A different finger that is between the fingers contacting the grip members 202 and 208 can alternatively be used. In described herein, in some examples, thumb 206 operates the thumb grip member 202, multiple fingers 216 (e.g., third finger, fourth finger, and fifth finger) operate the finger grip member 208, and index finger 220 operates the input control 230.

The input control 230 (and/or other input controls) can enable control of one or more functions of the teleoperated system. For example, the activation of an input control causes a control signal to be output by the input control, e.g., to a control system. The control system can be in the housing of the hand controller 200 or in a separate device in communication with the hand controller (e.g., as described for control system 150 of FIG. 1). In some examples, the control signal can cause activation of a particular function provided by a system in communication with the input control as described herein.

While the input control 230 may be attached to the central extension member 228 as shown, the input controls can be provided at any surface or portions of the hand controller 200, e.g., on one or more of the grip portions 202 and 208, on one or more of the extension portions 218 and 222 (e.g., at the proximal end of the hand controller or on a different portion of the surface of an extension portion), etc. In various implementations, various types of controls can be provided at any of various locations on the hand controller 200 to provide input signals based on physical manipulation of the controls by the user's hand, such as dials, knobs, buttons, sliders, trackpads or capacitive sensors, joysticks, trackballs, pivoting switches, etc.

In some implementations, the hand controller 200 can include one or more presence sensors that detect that a user's hand is engaged with and/or operating the hand controller 200. For example, optical sensors, pressure sensors, etc. can be used, e.g., at one or more of the grips 204 and 214, at the central extension member 228, and/or at other areas of the hand controller 200. For example, the presence sensors can be used to determine whether a user is operating the hand controller, while the input controls can be used to sense user input to cause activation of particular system functions. For example, presence sensors can provide safeguards against the hand controller 200 inadvertently dropping. In some examples, the thumb grip 204 and/or the finger grip 214 may include a sensing mechanism (not shown) that senses contact with the fingers of the user. In some implementations, the hand controller may include an accelerometer (not shown) that senses if the hand controller drops to the ground. The presence sensors and/or the accelerometer may detect if the hand of the user releases the hand controller 200. For safety, the hand controller 200 may then disengage or discontinue control of the slave devices of the teleoperated system 100.

In some implementations, the finger grip member 208 and/or thumb grip member 202 of the hand controller 200 may also include an extension member (not shown) that forms the proximal end 210 of the hand controller 200. The extension member can be a member that extends past the proximal end 210 shown in FIGS. 2 and 3 toward the palm of the hand, and may have a curved surface, spherical surface, and/or protrusions. The extension member can be contacted or cradled by the user's palm and/or fingers (e.g., third, fourth, or fifth fingers) in some implementations, to provide additional security in holding and manipulating the hand controller 200. In various implementations, the extension member may be integrated into grip member(s) of the hand controller 200, or removably coupled thereto and replaceable with other forms of extension members (e.g., differently-sized and/or differently-shaped).

The position and/or orientation of the hand controller 200 (or another portion of the hand controller 200) in space may be sensed, e.g., in a working environment or workspace of the hand controller 200. One or more sensors 234 can detect, and/or can enable the detection of, the position and orientation of the hand controller 200 in the working environment. In implementations where the hand controller 200 is mechanically ungrounded, the hand controller 200 is effectively unconstrained for both position and orientation motions within the user's reachable workspace and a sensing workspace. Some examples of sensing systems able to sense the position and orientation of the control body 202 are described above. Such a sensor tracks position and/or orientation of the hand controller 200 in a workspace (working environment) relative to a fixed reference point. In some examples, a sensor Cartesian coordinate system (Xs, Ys, Zs) may be generally centered at the sensor. In some applications, the reference coordinate system may be a finger grip coordinate system, such that any movements measured in the sensor coordinate system may be transformed by an applied transformation from the sensor coordinate system to the finger grip coordinate system.

Sensor 234 can be positioned at various locations on or in the housing of the hand controller 200. In some implementations, the hand controller 200 can include one or more sensors or sensor components operative to sense and/or assist an external sensor in detecting position and orientation of the hand controller 200. For example, motion sensors (accelerometers, gyroscopes, etc.) can be used within the hand controller 200 in some implementations. In various implementations, the sensor may be a six degree of freedom (6 DOF) electromagnetic (EM) sensor, an optical tracking sensor, a fiber optic shape sensor, or another type of sensor.

In some implementations, the hand controller 200 can include a component (e.g., sensor 234) that can be tracked by a sensing system that is located externally to the hand controller 200, e.g., one or more magnets, electromagnetic signal emitters, optical patterns, etc. In some implementations, the hand controller 200 can include a sensor receiving component that receives signals emitted by an external system to assist in determining position and/or orientation of the hand controller 200 in space. In some implementations, the hand controller 200 includes a sensor or sensor component for tracking its position and orientation in the workspace, and an external sensor system can perform such tracking (e.g., one or more cameras capturing video and/or motion occurring in the workspace, and a control system detecting and tracking the hand controller in the workspace by examining the captured video or recorded sensor data, etc.).

In some examples, the position, orientation, and/or motion of the hand controller 200 in three-dimensional space can be sensed to control operation of a teleoperated slave device. For example, position, orientation, and motion of the hand controller with respect to a reference position in three-dimensional space can be used to control a corresponding position, orientation, and motion of an arm assembly and/or end effector instrument of a slave device in its available workspace and degrees of freedom.

In some implementations, one or more physical connections, e.g., a tether connection such as a cable, may extend out of the hand controller 200 to connect the hand controller to a master control system. Various control signals from sensors of the hand controller 200 can be output via the tether connection, and/or various signals from a control system can be received. In some implementations hand controller 200 is not tethered by physical connections, and can communicate with the control system via wireless signal communications. For example, a wireless transmitter can be provided in some implementations within a grip member 202 or 208 or other portion of the hand controller 200, where the transmitter is configured to send wireless signals to a master control system based on position, orientation, and/or motion of the control body 201 in space, based on the thumb grip and the finger grip portions 204 in their degrees of freedom, and/or based on the activations of input controls of the hand controller.

Figure 10:
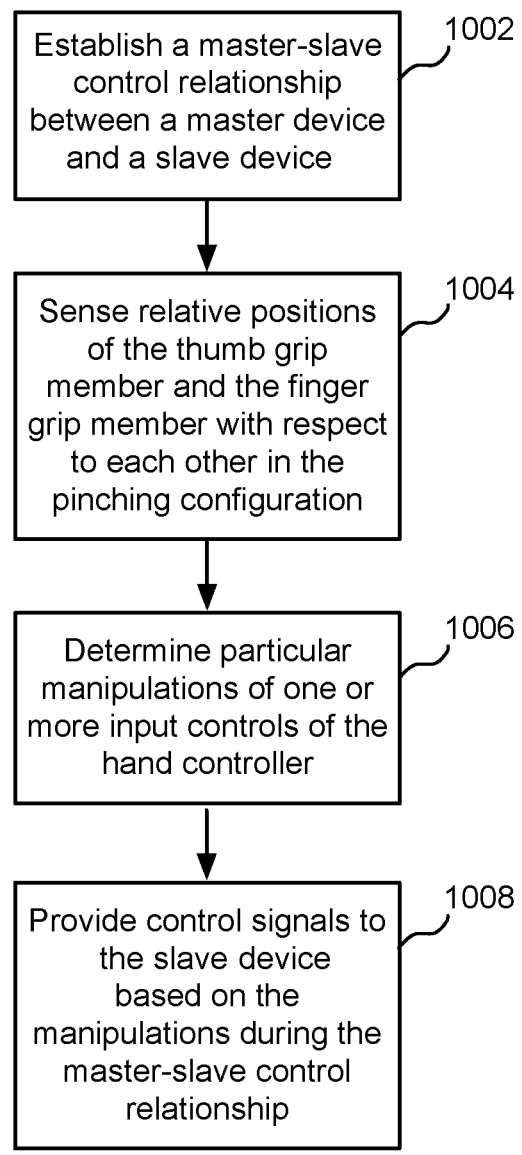
FIG. 10 is a flow diagram illustrating an example method for employing a master controller including one or more features described herein, according to some implementations.

Various functions described herein may be implemented using a computing system such as control system 1010 of FIG. 10. In some implementations, a computing system may be attached in a suitable location on the hand controller 200 (e.g., attached to the thumb grip member 202 on the opposite side to the thumb 206, attached to the finger grip member 208 on the opposite side to the fingers 216, attached beneath the central extension member 228, etc. In some implementations, the control system is implemented external to and communicates with the hand controller 200.

In some implementations, the hand controller 200 can be a mechanically grounded controller. For example, the hand controller 200 (or other hand controller implementations herein) can be coupled to a mechanical linkage that is coupled to the ground or an object connected to ground, providing a stable platform for the use of the hand controller 200. For example, grip members 202 and 208 of the hand controller 200 (or other hand controller implementations herein) can be coupled to a central body that extends between the grip members 202 and 208 toward the distal end 212 of the hand controller, and a grounded mechanical linkage can be connected to the central body. The mechanical linkage can provide six or more degrees of freedom to the hand controller. Some examples of such linkages are described below with reference to FIGS. 8 and 9, and in U.S. Pat. No. 6,714,839 B2, which is incorporated herein by reference.

FIG. 3 is another perspective view of the hand controller 200 of FIG. 2 being manipulated by a user's hand, according to some implementations. FIG. 3 shows an example of a side view of the hand controller 200 of FIG. 2.

In some implementations, the thumb grip member 202 and the finger grip member 208 are coupled together at the proximal end 210 to form a U-shaped unitary piece in which the thumb grip member 202 and the finger grip member 208 are configured to be moved toward or away from each other in the pinching configuration. In some implementations, the proximal end 210 of the hand controller 200 is at a central portion 302 of the hand controller 200, where the central portion 302 is positioned between the thumb grip member 202 and the finger grip member 208.

In some implementations, the thumb grip member 202 and the finger grip member 208 are formed together and are connected by a flexible portion in the central portion of the unitary member. The flex in the central portion 302 allows the grip members 202 and 208 to be pivoted toward and away from each other in pinching and releasing motions. In some implementations, the central portion 302 can be made thinner in width than the grip members 202 and 208 to which it is joined, e.g., to allow easier flexing.

In some implementations, the central portion 302, thumb grip member 202, and finger grip member 208 are separate members, and the grip members 202 and 208 are rotatably coupled to the central portion 302. For example, the grip members 202 and 208 can each be coupled to the central portion by a respective rotary coupling. In some implementations, thumb grip member 202 and finger grip member 208 are separate members that are rotatably coupled to each other without a separate central portion. Examples of the grip members 202 and 208 rotatably coupled to each other is described below with respect to FIGS. 4-6.

In various implementations, the central portion 302 and/or proximal ends of the grip members 202 and 208 are curved to ease contact with the palm of the hand. For example, surfaces at the furthest proximal point of the central point 302 are rounded. This allows fingertip control of the hand controller 200 with reduced interference from the proximal end with the hand. For example, the hand controller 200 can either be held slightly out from the palm to allow additional finger tip range of motion, or may be pulled into the palm for more security or more stable wrist motion control.

In some implementations, the input control 230 is a slider switch that slides from the force of the user's finger back and forth between the proximal end 210 and the distal end 212. Moving the slider to an activating position can cause a control signal to be output by the input control 230, e.g., to a control system. The control system can be in the housing of the hand controller 200 and/or in a separate device in communication with the hand controller (e.g., as described for control system 150 of FIG. 1). In some examples, the control signal can cause activation of a particular function provided by a system in communication with the input controls as described herein.

Figure 4:
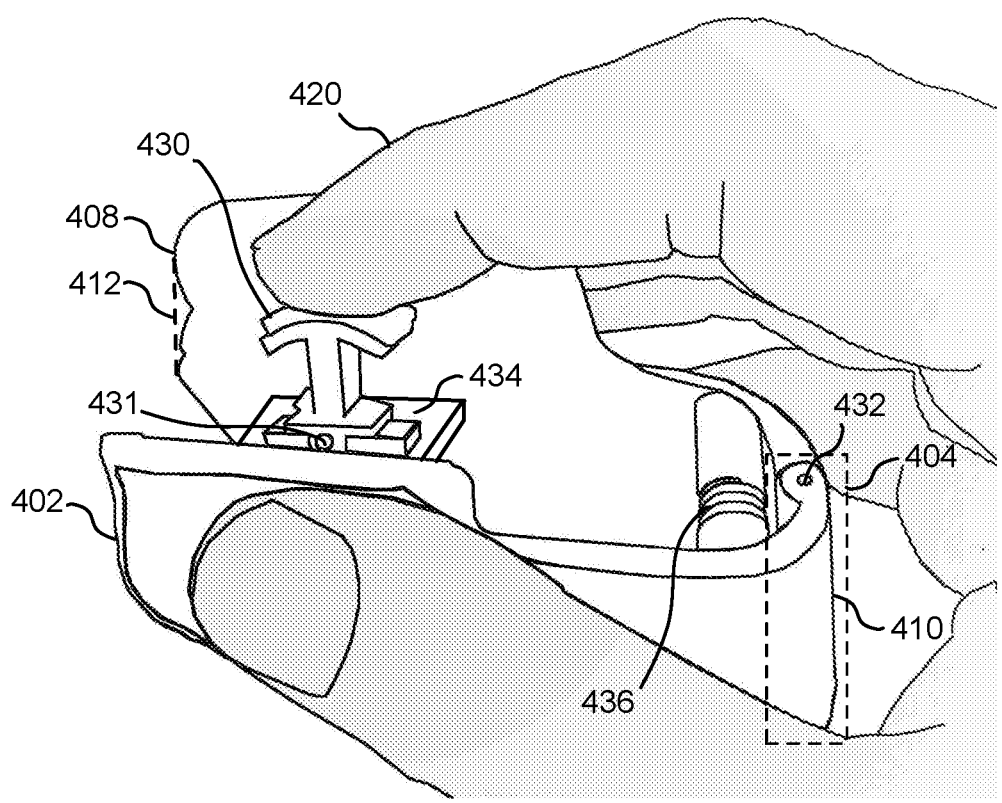
FIG. 4 is a perspective view of an example master controller that includes a control rocker being manipulated by a user's hand, according to some implementations.

FIG. 4 is a perspective view of an example hand controller 400 that includes a control rocker being manipulated by a user's hand, according to some implementations. In some implementations, the hand controller 400 includes a thumb grip member 402 engaged by a thumb and a finger grip member 408 engaged by multiple (non-thumb) fingers. The hand controller 400 also includes an input control 430. In this particular implementation, the input control 430 is a two-way control rocker that rocks or pivots back and forth toward either the proximal end 410 or the distal end 412 of the hand controller 400. As shown, the input control 430 can be rocked back and forth by the second finger 420 of the hand of a user. The input control 430 may be attached to a central extension member 434 that is coupled to the finger grip member 408 (or may be alternatively coupled to the thumb grip member 402).

In some implementations, the input control 430 pivots around a shaft or pin 431, and the position of the input control 430 in this rotary degree of freedom causes one or more control signals to be output by the input control 430, e.g., to a controller or system. In some examples, the control signal can cause activation of a particular function provided by a system in communication with the input control as described herein.

In some implementations, the input control 430 rocks forward and backward in order to activate two different functions associated with the forward and backward positions, respectively. In some examples, the forward and backward positions on the finger-contacted surface of the input control 430 can have different tactile features like bumps or ridges that distinguish the two positions tactilely, e.g., to distinguish two different functions (e.g., primary versus secondary energy). In some implementations, additional control positions can be provided in the rotary degree of freedom of the input control 430 to activate output of a different control signal associated with each control position.

In the implementation shown, the thumb grip member 402 and the finger grip member 408 are separate members that are rotatably coupled to each other at the proximal end 410 of the hand controller 400. In some implementations, the thumb grip member 402 and the finger grip member 408 are coupled to each other by a rotary coupling that provides rotation or pivoting around a pin 432, where the distal portions of the thumb grip member 402 and the finger grip member 408 move toward and away from each other when the fingers of the user pinch together or are moved apart.

In some implementations, the hand controller 400 may include a spring 436 (or other actuator) that exerts a restoring force on the thumb grip member 402 and the finger grip member 408. The restoring force causes the thumb grip member 402 and the finger grip member 408 to move away from each other and return to their (unactivated) neutral position if the fingers and thumb remove sufficient force that was applied in the pinching motion. As such, when the fingers of the user release from a pinching motion, the spring 436 causes the thumb grip member 402 and the finger grip member 408 to move away from each other. The sensor senses a distance between the thumb grip member and the finger grip member. In some implementations, the thumb grip member 402 is movable in a first degree of freedom and the finger grip member 408 is movable in a second degree of freedom, and the sensor senses respective positions of the thumb grip member and the finger grip member in the first grip degree of freedom and the second grip degree of freedom.

Figure 5:
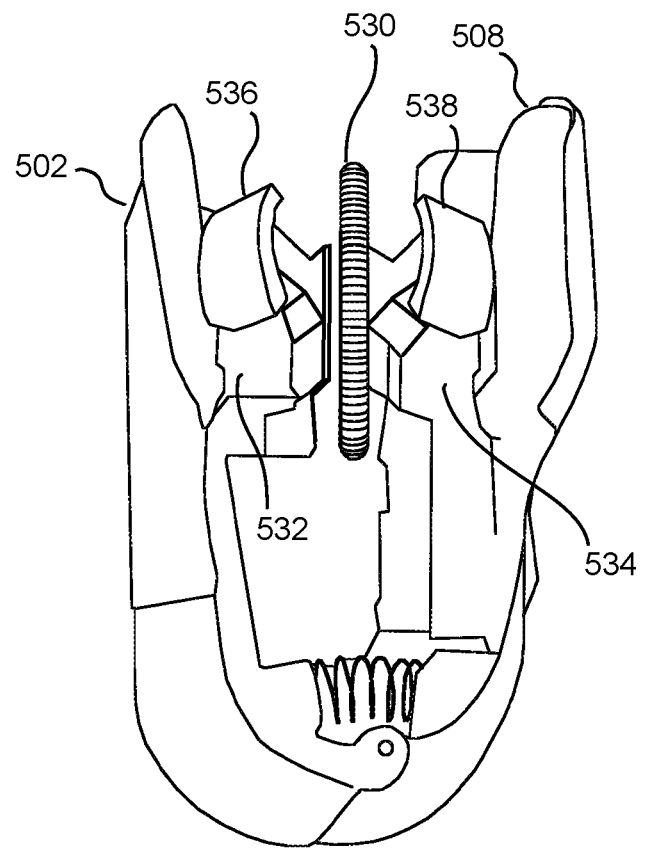
FIG. 5 is a perspective view of an example master controller that includes a control wheel, according to some implementations.

FIG. 5 is a top perspective view of an example hand controller 500 that includes a control wheel, according to some implementations. In some implementations, the hand controller 500 includes a thumb grip member 502 and a finger grip member 508. The hand controller 500 also includes an input control 530. In this implementation, the input control 530 is a control wheel that is positioned between the thumb grip member 502 and the finger grip member 508. The input control 530 rotates around an axle (not shown). In some implementations, as shown in FIG. 5, the axle can be rotatably coupled to a central extension member 534 that is coupled to the finger grip member 508. In other implementations, the axle may be rotatably coupled to a central extension member 532 that is coupled to the thumb grip member 502. As such, the input control 530 is coupled to either the thumb grip member 502 or the finger grip member 508 via a central extension member.

In some implementations, the position of the input control 530 causes a control signal to be output by the input control 530, e.g., to a controller or system. In some examples, the control signal can cause activation of a particular function provided by a system in communication with the input control as described herein. In various implementations, the input control 530 or control wheel can be rotated by a user's finger to provide a user-adjusted control signal based on the position or motion of the input control 530 that can be used to cause adjustment of parameters or functions of the teleoperated system 100, scroll displayed information on a display screen, etc. For example, in some implementations, the input control 530 may be rotated to control continuous and discrete settings such as brightness, energy levels, volume, etc. Input control 530 may also serve as a button to access the menu system and activate selected menu options. In some implementations, the input control 530 may include detents in its rotary degree of freedom to provide haptic feedback to the user rotating the input control. In some implementations, the input control 530 may be accessed by a finger (e.g., second finger or index finger) on one side of the controller (e.g., the top when used in an orientation similar to FIG. 4), or may be accessed by the thumb of the operating hand from the opposite side of the controller (e.g., the bottom of the controller).

Also included in some implementations are input controls 536 and 538, where input control 536 is a rocker switch attached to a first central extension member 532, and input control 538 is a rocker switch attached to a second central extension member 534. A gap can be provided between the control wheel 530 and the rocker switch that is coupled to the grip member not coupled to the control wheel, to allow the grip members 502 and 508 to be moved toward each other in a pinching motion. Each input control 536 and 538 can control different functions. In some implementations, the input controls 536 and 538 may have different surface geometry and/or physical features on the portions that contact the user's finger, e.g., to distinguish them from each other (e.g. concave versus convex surface, etc.). In some implementations, the input control 530 can function as a physical partition between the other input controls 536 and 538, e.g., to allow the user to feel the side of the input control 530 with an operating finger and thereby identify the rocker switch 536 or 538 that is being touched with the finger.

Figure 6:
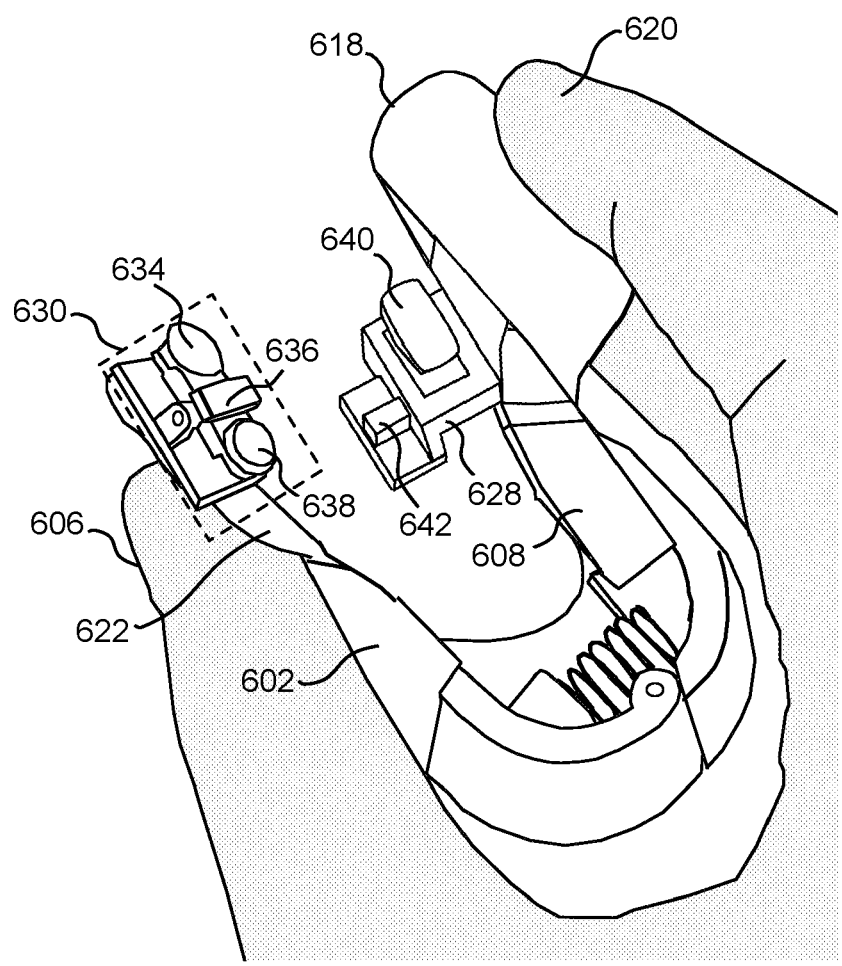
FIG. 6 is a perspective view of an example master controller being manipulated by a user's hand and that includes an input control on a thumb grip member, according to some implementations.

FIG. 6 is a top perspective view of an example hand controller 600 that includes input controls on the thumb grip member being manipulated by a user's hand, according to some implementations. In some implementations, the hand controller 600 includes a thumb grip member 602 with a thumb grip extension portion 622 and a finger grip member 608 having a finger grip extension portion 618, similar to other implementations herein, e.g., as shown in FIG. 4.

The hand controller 600 includes an input control 630 attached to the thumb grip member 602. As shown, the input control 630 is coupled to the thumb grip member 602 on a side of the thumb grip member 602 that is opposite to the grip side of the thumb grip member 602 that is engaged by the thumb 606. In some implementations, input control 630 is attached to the thumb grip extension portion 622 on a side of the extension portion 622 that is opposite to the side of the extension portion 622 that is adjacent to the thumb 606. For example, the thumb grip extension portion 622 partially curves over the thumb grip where thumb 606 is engaged, and the input control 630 is positioned on the curving portion so as to be accessible to second finger 620 from the top of the controller 600.

In this example implementation, the input control 630 includes multiple controls such as buttons 634 and 638. Such buttons may have various functions. In this example, buttons 634 and 638 can control energy functions, e.g., a cut function (e.g., actuated by a press motion on control 634) and a coagulate/bipolar function (e.g., actuated by a press motion on control 638). In this example, a bar or ridge 636 is positioned between the buttons 634 and 638 which can provide a tactile reference feature for the user's finger that activates the buttons 634 and 638. For example, the bar 636 can have a surface that is at a higher elevation than the buttons 634 and 638 so that the user's finger 620 will contact the bar 636 first, before contacting either button 634 or button 638. This allows the bar 636 to serve as a "home" feature or surface, allowing the user to orient their finger in a tactile fashion at the home position on the bar 636 and then select the desired button in front of or in back of the bar 636.

In this example, these energy function buttons 634 and 638 are positioned on thumb grip member 602 near the thumb 606 so that actuation of the buttons by the user's hand is less coupled to the grip of the user's hand on the controller 600. For example, the user can actuate these buttons, e.g., with finger 620, with less disruption to the position and/or orientation of the hand controller 600 in space, and/or less disruption to the grip positions relative to each other (e.g., the angle between the grip members 602 and 608), e.g., due to the biomechanics of the human hand. Another advantage of locating input controls 634 and 638 on the thumb grip member 602 is that the controls 634 and 638 are easier to find for the user's finger 620 via proprioception, due to the user bringing the finger tip or finger pad of finger 620 to an area near the user's thumb 606. Users may intuitively know the position of their thumb and can thus locate areas and activate controls near the thumb with greater ease using a finger such as finger 620.

In some implementations, hand controller 600 can also or alternatively include other input controls. For example, a rocker switch 640 and a button 642 can be located on a central extension member 628 that is connected to the finger grip portion 618. In various implementations, various functions can be associated with activation of these input controls. In this example, rocker switch 640 can be rotated about a pivot axis to different positions. For example, two positions of the switch can be a forward position to which the switch is pushed by the user's finger (closer to the distal end of the controller 600) and a back position to which the switch is pulled by the user's finger (closer to the proximal end of the controller 600). In one example, the forward position can activate a swap function to swap control between teleoperated arms of a slave device, and the back position can activate a clutch function which causes the controller to enter controlling mode or non-controlling mode (e.g., described with reference to FIG. 10). In another example, button 642 can control a camera function (e.g., actuated by a press motion), e.g., to toggle a camera mode of the controller in which manipulations of the hand controller 600 can control movements of an image capture device, e.g., a camera, at a work site (e.g., a surgical site). The particular function may vary depending on the particular implementations.

In some implementations, the activation of the input control 630 causes a control signal to be output by the input control 630, e.g., to a controller or system. In some examples, the control signal can cause activation of a particular function provided by a system in communication with the input control as described herein.

Figure 7:
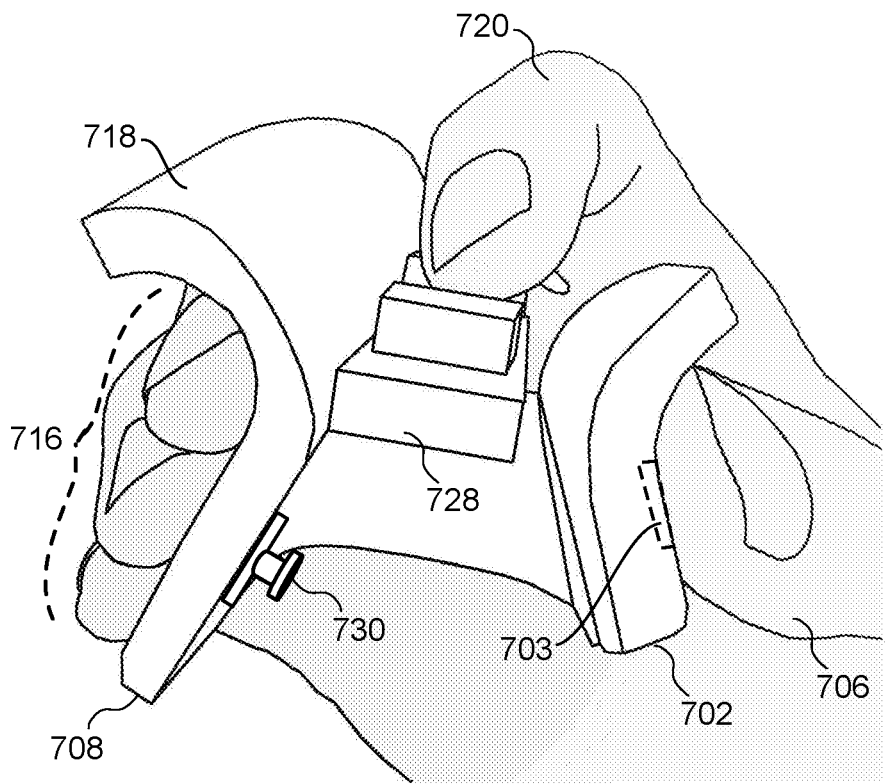
FIG. 7 is a perspective view of another example master controller, according to some implementations.

FIG. 7 is a perspective view of an example hand controller 700 that includes an input control on a finger grip member being manipulated by a user's hand, according to some implementations.

The hand controller 700 includes a thumb grip member 702 and a finger grip member 708. In this example, the hand controller 700 includes an input control 730. In some implementations, the input control 730 is a control button, or can be another type of input control (rocker switch, sliding switch, etc.). Activation of (e.g., depressing) the input control 730 causes a control signal to be output by the input control 730, e.g., to a controller or system. In some examples, the control signal can cause activation of a particular function provided by a system in communication with the input control as described herein. For example, the button of the input control 730 can be pressed to send a control signal to the control system to activate an associated function of the connected system, e.g., teleoperated system 100 of FIG. 1.

In this implementation, the input control 730 is attached to the finger grip member 708. As shown, the input control 730 is coupled to the finger grip member 708 on the side of the finger grip member 708 that is opposite to the side of the finger grip member 708 that is engaged by the fingers 716. In some implementations, as shown, the input control 730 is positioned on a low portion (e.g., lower half) of the finger grip member 708 (with reference to the controller orientation of FIG. 7), e.g., underneath a central extension member 728. This can reduce accidental actuation of the input control 730 by the second finger 720, and/or can reduce clutter in the presentation of multiple input controls of the hand controller 700.

In various implementations, the thumb 706 can be used to contact and activate the input control 730 (and/or other input controls within reach of the thumb). For example, the thumb 706 is pulled away from finger grip member 702 and moved underneath the hand controller 700 to access the input control 730. In some implementations, the thumb grip member 702 can be made shorter in the vertical dimension than the finger grip member 708, and the input control 730 can be positioned on the lower portion of finger grip member 730 that extends past the bottom of the thumb grip member 702, so that the thumb 706 can easily move over to the input control 730. The thumb 706 can be easily and safely pulled away from the thumb grip of the thumb grip member 702 and moved underneath the controller 700, because the fingers 716 and 720 securely hold the other portions of the hand controller 700, and the finger-side extension portion 718 can improve this holding of the controller (as described above) when the thumb is lifted off. In some cases, e.g., if the user has moved the proximal end of the hand controller 700 toward the palm of the hand to contact the palm, the palm additionally secures the controller 700 in the hand and allows the thumb 706 to be moved away from thumb grip member 702.

In some implementations, one or more input controls can be provided on controller 700 (or other controller implementations herein) that can be accessed and actuated by both the thumb and one or more other fingers of the hand, e.g., the second finger 720. For example, the control wheel 530 of FIG. 5 can be accessed by the thumb from one side of the controller (e.g., below the wheel in the orientation of FIG. 7), and accessed by the second finger from the opposite side of the controller (e.g., above the wheel in the orientation of FIG. 7). Other types of controls can allow such access from opposite sides of the controller, e.g., trackballs, optical sensors, switches, etc.

In some implementations, the thumb grip member 702 can include an input control 703, e.g., a presence sensor such as an optical sensor, touch sensor, etc., that senses the presence of the thumb 706 contacting the grip member 702. The presence sensor can detect the removal (or removed state) of the thumb 706 from the thumb grip member 702 and can send out an input control signal that activates a system function based on this detection.

For example, the thumb presence sensor can be a clutch control, where the action of disengaging the thumb 706 from the grip member 702 causes the system in a controlling mode to enter a non-controlling mode in which a master-slave control relationship is ceased, e.g., user movements (or other manipulations) of the controller 700 do not cause movements of an associated slave device in the non-controlling mode (examples described below with respect to FIG. 10). Engaging the thumb 706 causes the system re-enter controlling mode. In some implementations, the action of disengaging the thumb 706 from the grip member 702 can cause the system to enter a more persistent non-controlling mode in which explicit command(s) are required to be input by the user for the system to re-enter controlling mode, e.g., a command provided to the control system via a different input control of the controller 700 (e.g., a switch, button, etc.), or a command provided to the control system via a different input device (e.g., a foot pedal or other foot control, a separate sensor that senses the user or a portion of the user such as the user's head, gaze, etc.). In addition, any of the clutch functions described herein can alternatively be implemented as functions that enter this type of persistent non-controlling mode. In some implementations, for example, controlled jaws or grip of a slave instrument can be kept in a closed state, regardless of controller manipulation, if the thumb is removed from the thumb grip member and a non-controlling mode is entered. Such clutch functionality and/or persistent non-controlling mode functionality can also or alternatively be implemented by presence sensors at various other locations on the hand controller in implementations described herein, e.g., for a presence sensor on finger grip member 208 or other members and controls of the hand controller.

In some implementations, the thumb presence sensor can be used to enable one or more functions, or multiple different functions, for input controls of the controller 700. In one example, input control 730 on the controller 700 (e.g., a joystick control, rocker switch, control wheel, or other type of control) can control functions such as user interface functions in a displayed graphical user interface of the system (e.g., telemanipulator system) if the thumb is sensed as being disengaged from the thumb grip member by the thumb presence sensor 703. In this example, this sensed disengagement of the thumb also causes the system to enter a non-controlling mode, so that the user's thumb is free to activate the input control 730 (or other input control) without controlling motions of a slave device. While the thumb is engaged with the thumb grip member, the input control 730 can be disabled, or can control other functions of the system (e.g., system settings such as display device brightness, scaling of controller movement to slave movement, etc.). In another example, a control wheel (e.g., as in FIG. 6) can control user interface functions in a displayed graphical user interface while the thumb is contacting the finger grip of the thumb grip member (e.g., the second finger can actuate the control wheel). When the thumb is sensed to be disengaged, the control wheel can control different functions, e.g., a swap function, camera control toggle, etc.

In some implementations of the controllers described herein, one or more input controls can be enabled to activate different functions depending on the particular finger that is detected to be actuating the input control. In some examples referring to controller 700, a thumb presence sensor 703 on thumb grip 702 and/or one or more finger presence sensors on finger grip 708 can be used to detect whether the thumb and/or other fingers are engaged with their respective grip members and thus whether the thumb and/or other fingers are actuating input controls. For example, one function can be associated with a particular finger that is detected activating the input control (e.g., the second finger), and a different function can be associated with a different finger (e.g., thumb) detected to be activating the input control. For example, the control wheel 530 of FIG. 5 can be configured to control a first set of functions when it is activated by the second finger, and control a second, different set of functions when thumb activation of the control wheel 530 is detected. In some examples, the thumb is considered to be actuating the input control if the thumb is not detected to be engaged with thumb grip member, and the second finger is considered to be actuating the input control if the thumb is detected to be engaged with thumb grip member. In some implementations, additional sensors can be used, e.g., optical or pressure sensors on different sides and/or on different contacted portions of the input control to detect whether the input control is being contacted and actuated from one side or the opposite side of the controller, thus indicating whether thumb or second finger is actuating the input control.

Figure 8:
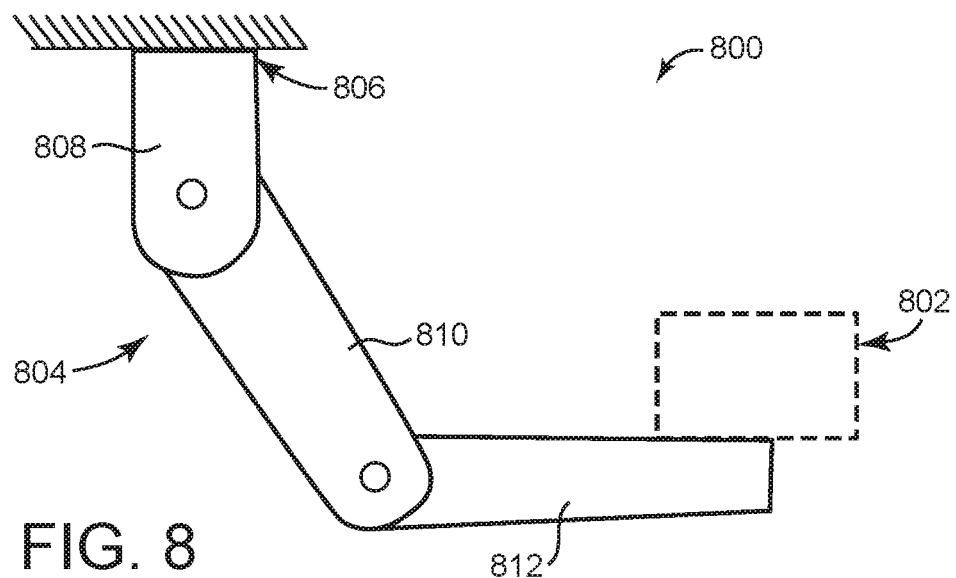
FIG. 8 is a schematic illustration of view of an example controller system that is mechanically grounded.

FIG. 8 is a schematic diagram of an example controller system 800 that is mechanically grounded, and which can be used with one or more features described herein for a master controller. Controller system 800 includes a control portion 802 that can be engaged by a user's hand. The control portion 802 includes a hand controller portion that can include one or more features described herein, as well as one or more mechanisms. Some examples of control portion 802 are described in greater detail below with respect to FIG. 9.

Control portion 802 is coupled to a serial kinematic chain 804. The proximal end 806 of the chain 802 is mechanically grounded. In this example, the kinematic chain 806 includes three members 808, 810, and 812 that are rotatably coupled to one or more other members of the chain 806 by rotational couplings having rotational axes. For example, member 808 is mechanically grounded at a first end 806 of member 808 and is rotatably coupled to member 810 at a second end of member 808. Member 810 is rotatably coupled to member 808 at a first end of member 810 and rotatably coupled to member 812 at a second end of member 810. Member 812 is rotatably coupled to member 810 at a first end of member 812 and coupled (e.g., rotatably coupled) to control portion 802 at a second end of the member 812. The rotational axes of the chain 804 can be sensed and/or driven by sensors and/or actuators. Some implementations can provide additional actuated and/or sensed motion of the kinematic chain, e.g., about axes extending lengthwise through one or more members 808, 810, and 812.

Figure 9:
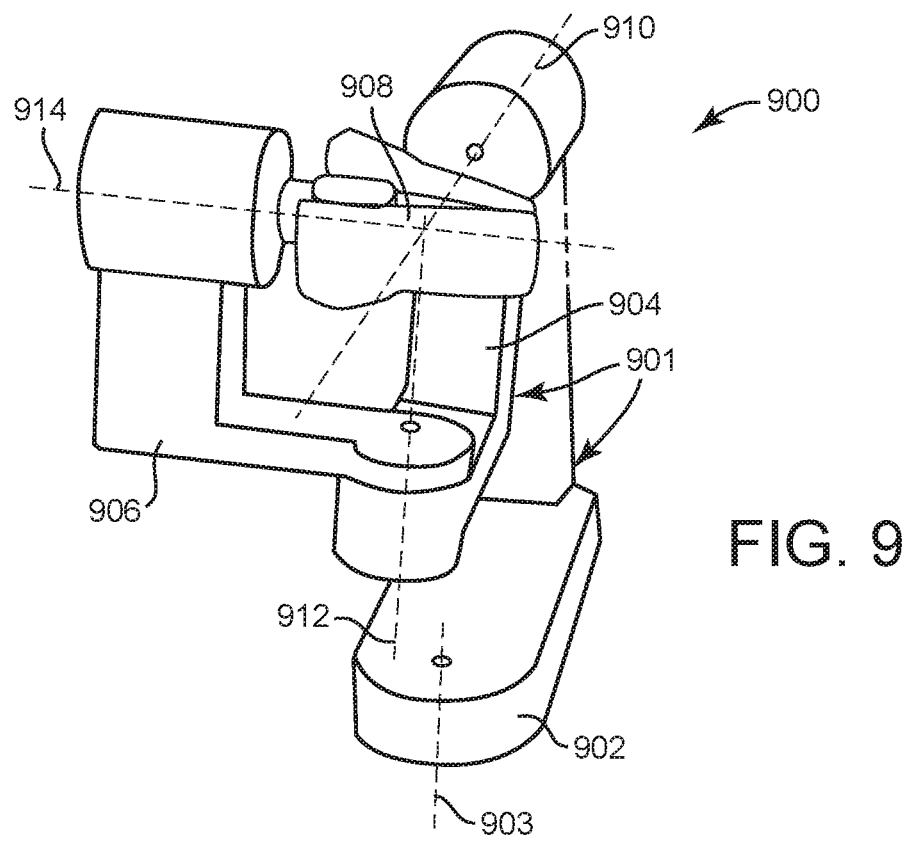
FIG. 9 is a perspective view of an example master control portion that is mechanically grounded and can be engaged by a user.

FIG. 9 is a perspective view of an example control portion 900 that is mechanically grounded and can be engaged by a user. In some examples, control portion 900 can be the control portion 802 of the controller system 800 of FIG. 8. In some implementations, control portion 900 can be coupled to a different kinematic chain or other structure that is mechanically grounded.

In this example, control portion 900 includes members of a serial kinematic chain 901 that includes three members 902, 904, and 906 that are rotatably coupled to one or more other members of the chain 901 by rotational couplings having rotational axes.

Control portion 900 can be coupled by a rotational coupling at a first end of member 902 to the second end of member 812 of the kinematic chain 804, allowing rotation about axis 903 between members 812 and 902. Member 902 is rotatably coupled to member 904 at a second end of member 902. Member 904 is rotatably coupled to member 902 at a first end of member 904 and rotatably coupled to member 906 at a second end of member 904. Member 906 is rotatably coupled to member 904 at a first end of member 906 and coupled (e.g., rotatably coupled) to a hand controller portion 908 at a second end of the member 906. The rotational axes of the chain 901 can be sensed and/or driven by sensors and actuators.

Hand controller portion 908 can include features which can be contacted by a user, e.g., a hand of a user. For example, a handle, extension member, grips, switches, and/or other features described herein, e.g., with respect to FIGS. 2-7, can be provided on hand controller portion 908.

In some implementations, the hand controller portion 908 is coupled at a distal end of a serial kinematic chain that includes members 906, 904, 902, 812, 810, and 808, with the proximal end 806 of the chain mechanically grounded. This provides a stable platform for the use of the hand controller portion 908.

In some implementations, the kinematic chain 901 forms a gimbal mechanism that allows the hand controller portion 908 to be rotated about the rotational axes of the chain 901, e.g., axes 903, 910, 912, and 914. Hand controller portion 908 can also be translated in at least three linear degrees of freedom allowed by the kinematic chain formed by kinematic chains 804 and 901.

Various kinematic chains, linkages, gimbal mechanisms, flexible structures, or combinations of two or more of these can be used with the mechanically grounded hand controller in various implementations to provide one or more degrees of freedom to the hand controller. Some further examples of linkages and/or gimbal mechanisms that can be used with hand controller portion 908 are described in U.S. Pat. No. 6,714,839 B2, incorporated herein by reference.

FIG. 10 is a flow diagram illustrating an example method 1000 for employing a hand controller including one or more features described herein, according to some implementations. In some implementations, the method can, for example, be used with an example teleoperated system or other control system in which the hand controller is a master controller that controls a slave device. For example, in some implementations, the hand controller is an ungrounded master controller, e.g., the hand controller 200 of FIG. 2 or the hand controllers shown in other figures, and a method can be performed by a control circuit component of the master control device 122, e.g., performed by control system 150. In some implementations, the hand controller is a grounded master controller. In some examples, the control circuit can include one or more processors, e.g., microprocessors or other control circuits, some examples of which are described below with reference to FIG. 10. A single master controller is referred to in the method for explanatory purposes. The master controller can be, for example, any of the controller implementations described herein. Multiple master controllers can be similarly processed as described in the method. Other implementations can use a hand controller having one or more features described herein with other types of systems, e.g., non-teleoperated systems, a virtual environment (e.g., medical simulation) implemented on a processing device and having no physical slave device and/or no physical subject interacting with a physical slave device, etc.

In block 1002, a master-slave control relationship is established between a master device (such as an ungrounded hand controller) and a slave device, such as a slave device or instrument, in some examples. In some implementations, the master-slave relationship may be established by a controlling mode of the hand controller. For example, this control relationship can be established in response to receiving a control signal from the hand controller or a different component of the system that indicates that the hand controller is to enter a controlling mode (e.g., following mode). In the established control relationship, positions and orientations of the hand controller are sensed as described herein, and can be described in signals that are transmitted to a control system, e.g., in the controller, slave device, and/or a separate control system. In some examples, motion of the hand controller in space causes corresponding motion of a controlled instrument of the slave device, and/or can control other functions of the slave device.

As indicated herein, a finger grip member and the thumb grip member couple or join at a proximal end of the master device and both extend toward a distal end of the master device. A thumb grip of the thumb grip member is receptive to a thumb of a hand of a user. A finger grip of the finger grip member is receptive to fingers of the hand of a user.

In block 1004, relative positions of the thumb grip member and the finger grip member are sensed with respect to each other in the pinching configuration. As indicated herein, the finger grip member includes a finger grip receptive to multiple fingers of the hand of the user, and where the thumb grip member and the finger grip member are movable within a pinching configuration with respect to each other. In some implementations, the positions of the thumb grip member and the finger grip member are sensed in their respective degrees of freedom. These positions can be described in signals that are transmitted to a control system, e.g., in the controller, slave device, and/or a separate control system.

In block 1006, manipulations of one or more input controls of the hand controller are determined. Such determination can occur in a controlling mode (during the established control relationship). For example, the user's hand may activate the input controls as described herein and the activations are sensed by the input controls. These input control activations can be described in signals that are transmitted to a control system, e.g., in the controller, slave device, and/or a separate control system. In various implementations, input controls of the hand controller can be manipulated by the user's hand to provide control signals to the control system and/or to the slave device. As described herein, such input controls can include buttons, wheels, switches, presence sensors, joysticks, trackballs, knobs, trackpads, etc.

In block 1008, slave control signals are provided to the slave device based on the manipulations during the master-slave control relationship. For example, the slave control signals may be provided from a control system that received controller signals from the hand controller, where the slave control signals cause one or more functions of the slave device to be activated, e.g., slave actuators controlled to output forces to move arm, instrument, and end effector components, irrigate or suction functions, energy application, etc. As indicated herein, in various implementations, the hand controller's control signals cause changes in associated state(s) or activations of associated functions of the controlled slave device.

The blocks and operations described in the methods disclosed herein can be performed in a different order than shown and/or simultaneously (partially or completely) with other blocks and operations, where appropriate. Some blocks and operations can be performed for one portion of data and later performed again, e.g., for another portion of data. Not all of the described blocks and operations need be performed in various implementations. In some implementations, blocks and operations can be performed multiple times, in a different order, and/or at different times in the methods.

In some additional examples, input controls can provide control signals to provide input to a displayed user interface, virtual environment, or other display provided by a display device, e.g., a user interface displayed on a display device 126 of FIG. 1. In some examples, sliding finger switch 230 (or other input control on the various hand controller implementations) can be a clutch control, where, for example, pulling the switch toward a position toward the proximal end of the hand controller (and/or maintaining the switch at that position) provides a clutch function to enter controlling mode (following mode) with the hand controller. In some implementations, pushing the switch 230 to a position closer to the distal end of the hand controller can exit the hand controller from controlling mode and cause it to enter non-controlling mode, or cause activation of a different function (e.g., camera control mode in which motion of the hand controller controls a camera of the slave device, a user interface mode in which input from the input controls is provided to a displayed user interface, etc.).

Movement and orientation of the hand controller and activation of input controls are sensed by various sensors as described above, and sensor signals are sent to a controller (e.g., control system 150) in response to the sensing. The controller activates one or more selected functions of a plurality of functions provided by a system in communication with the hand controller. For example, a control system 150 or control module can send commands to other system components to activate one or more functions based on the sensor signals received from the hand controller.

The term "function" as used herein can include one or more actions or outputs (including operations or motions) of a controlled device such as a slave device. For example, a surgical slave device may include surgical instruments as described above, and a function can include one instrument action or multiple instrument actions (e.g., actions performed serially and/or at least partially in parallel). In some implementations, a function can be a category of actions performed by a slave instrument. In some examples, a cutting tool such as a knife or a surgical scissors may perform various actions in the category of cutting. In some implementations, the input control activating a function causes one or more actions associated with the activated function to be performed. For example, a cutting function can include one or more actions such as moving a scalpel to create an incision in a surgical site with a straight cut. Alternatively, the cutting function can include actions such as snipping a blood vessel with a surgical scissors, to be cauterized.

Surgical instruments may include cutting tools, grasping tools, cauterizing tools, irrigation tools, suction tools, absorbing tools, etc. In some implementations, the hand controller (or control system) outputs teleoperation control signals based on the sensor signals to control functions including movements of the surgical instruments, and/or mechanical arms holding the surgical instruments, in communication with the hand controller. Various functions can be associated with such controlled instruments or tools, including irrigation (injecting a liquid into or onto a surgical site or other location), suction (removing of such liquid), clutch (disengage control of slave device manipulator arms, e.g., to allow master controllers to be repositioned without such control), turning on or off a camera (capture or record a scene at a physical location such as a surgical site), outputting energy by a cutting tool to cut or seal biological tissue, etc.

Some examples of functions can include, for example, a swap function for a button allowing control of a first telemanipulator arm or instrument to be swapped to a second arm or instrument; a camera function and/or clutch function for a slider switch (e.g., one function for one switch position, the other function for the other switch position); a user interface scroll function for a control wheel allowing scrolling of displayed interface elements (e.g., displayed on a display device); and energy output for surgical instruments mapped to input controls (e.g., control sliders, control rockers, control wheels, control buttons, etc.). In some implementations, particular functions of a teleoperated slave device can be mapped to the activation of the finger controls of hand controller 200, and such functions can be re-mapped to other functions of the slave device, e.g., based on a different mode of operation, commands received by the slave device, etc.

In some implementations, an input control may be activated by the user (e.g., in block 1006) to cause a control signal to be sent and cause activation of a function associated with the input control (e.g., in block 1008). In some implementations, the input control is operative to maintain output of the control signal to the system while the input control continues to be activated based on continued user input at the input control (e.g., a button is required to continue to be pressed in order to maintain output of the control signal to the system). In some implementations, the maintained output of the control signal causes the selected function to continue being activated by the system. For example, electrical energy may be applied to perform a coagulate function while an input control button is pressed. In some implementations, an audio signal may be output by the control system to indicate the energy is being applied. In another example, a clutch function and non-controlling mode may be activated and maintained while an input control button is pressed and maintained in pressed state, while controlling mode is active while the button is released. In another example, camera control may be activated as an input control button is continually pressed to allow the hand controller to control camera position and/or orientation, and the button is released (deactivated) to return the hand controller back to controlling the position and/or grip of a surgical grasping instrument and not control the camera position and orientation.

In some implementations, an input control on the hand controller can be used as a toggle to enter or exit control modes. For example, the input control button is pressed and released once to enter camera mode, and is again pressed and released to return to instrument control mode. In another example, the input control can be used to toggle (swap or switch) the arm or instrument being controlled by a hand controller, e.g., switch control to a different manipulator arm on a slave device. In some implementations, the input control may be used to deselect and/or deactivate a function, e.g. using a deselect toggle. In some implementations, the input control can be used as a trigger to initiate a sequence of functions or actions, e.g., a staple sequence of a stapler instrument.

In some implementations, a user interface (UI) and/or status readout can be displayed on one or more display devices of the system (e.g., display screens, virtual reality or augmented reality headsets or goggles, etc.). The user interface can display information related to operation of the hand controller.

In some implementations, actuators can be included in the hand controller to actively output forces on the hand controller, e.g., motors, voice coils, etc. In some examples, such forces can be used to alert the user to particular conditions of the hand controller, of the procedure, etc. For example, a vibration alert can be output by one or more actuators of the hand controller (e.g., a motor rotating an oscillating element), where a vibration force is transmitted to the hand operating the hand controller. In some examples, the vibration alert can be output in response to collisions that have occurred between controlled slave instruments and other objects, in response to a controlled instrument or arm reaching a limit to motion, as a safety alert when using a cutting or energy-outputting instrument, etc. In some implementations, distinct vibration signatures can be provided in association with different respective alerts (e.g., different vibration frequencies and/or amplitudes). Other types of forces can be used for such alerts in some implementations, e.g., single pulses of force, etc.

In some implementations, output such as haptic feedback on the hand controller (e.g., on the grip members 204) and/or visual displays on a display device can be provided by the system to assist user operation of the teleoperated surgical system. For example, a user interface may display warnings and/or error feedback on a display device, and/or audio output can be provided to indicates such warnings or errors. Such feedback can indicate functions that are potentially dangerous to a patient, and/or that a function to be activated is not appropriate (e.g., according to steps of a stored predetermined procedure) based on previous hand controller movement or previous function(s) activated.

In various implementations, other types of computer-assisted teleoperated systems can be used with one or more hand controller features described herein, in addition to surgical systems. Such teleoperated systems can include controlled slave devices of various forms. For example, submersibles, bomb disposal units, industrial applications, applications in hostile environments and worksites (e.g., due to weather, temperature, pressure, radiation, or other conditions), general robotics applications, and/or remote-control applications (e.g., remote controlled vehicle or device with a first-person view), may utilize teleoperated systems that include slave devices for sensory transmission (conveyed visual, auditory, etc. experience), manipulation of work pieces or other physical tasks, etc., and may use mechanically grounded and/or ungrounded master controllers to remotely control the slave devices. Any such teleoperated systems can be used with the various hand controller features described herein.

FIG. 11 is a diagrammatic illustration of an example teleoperated slave device and patient site 1100 for an example teleoperated surgical system, which can be used with one or more features disclosed herein according to some implementations.

A manipulator slave device 1102 can be controlled by one or more master controllers of a master control device. For example, one or more master control devices 122 as shown in FIG. 1 can be used to control slave device 1102, or one or more hand controller described herein. During a surgical procedure, the slave device can be positioned close to an operating table and patient (or simulated patient) for surgery, where it can remain stationary until a particular surgical procedure or stage of a procedure is completed. Slave device 1102 can include one or more arm assemblies 1114, 1116, and 1118. In some examples, each of these arm assemblies may include a surgical instrument 1124, 1126, and 1128, respectively. Each surgical instrument can include a surgical end effector, e.g., for treating tissue of the patient. The arm assemblies 1114, 1116, and 1118 can be configured to hold an image capturing device, e.g., an endoscope 1130, camera, or the like, which can capture images depicting a surgical site or portion thereof. The endoscope can be in communication with to one or more display devices and transmit images to the display devices, such as display device 126 of FIG. 1, a display device 1132 coupled to the slave device, and/or other display devices.

In this example, the arm assemblies may be caused to move and articulate the surgical instruments in response to manipulation of the master controller(s). This enables the user to direct surgical procedures at internal surgical sites through minimally invasive surgical apertures. For example, one or more actuators coupled to the arm assemblies can output force to cause links or other portions of the arm assemblies to move in particular degrees of freedom in response to control signals provided by the master controllers. The master controllers can be used within a room (e.g., an operating room) that also houses the slave device and worksite (e.g., within or outside a sterile surgical field close to an operating table), or can be positioned more remotely from the slave device, e.g., at a different room, building, or other location than the slave device.

Some implementations of the teleoperated system can provide different modes of operation. In some examples, in a non-controlling mode (e.g., safe mode) of the teleoperated system, the controlled motion of manipulator slave device 1102 is disconnected from the master controllers of the workstation in a disconnected configuration, such that movement and other manipulation of the master controls does not cause motion of the manipulator slave device. In a controlling mode of the teleoperated system (e.g., following mode), the motion of the manipulator slave device can be controlled by the master controllers such that movement and other manipulation of the master controllers causes motion of the manipulator slave device, e.g., during a surgical procedure.

In some implementations, the teleoperated surgical system can include a support on which a user, e.g., an operator such as a surgeon, can rest his or her forearms while gripping two grounded master controllers. For example, the master controllers can be positioned in a workspace disposed inwardly toward a patient, beyond the support.

Features disclosed herein may be implemented in various ways, including teleoperated and, if applicable, non-teleoperated (e.g., locally-controlled) implementations. Implementations on da Vinci® Surgical Systems are merely exemplary and are not to be considered as limiting the scope of the features disclosed herein. For example, different types of teleoperated systems having slave devices at worksites can make use of actuated controlled features described herein. Non-teleoperated systems can also use features described herein.

In some implementations, a controlled slave manipulator device can be a virtual representation of device, e.g., presented in a graphical simulation provided by a computing device coupled to the teleoperated system 1100. For example, a user can manipulate hand master controllers and foot controller(s) to control a displayed representation of an end effector in virtual space of the simulation and control virtual functions of the representation (or other virtual instruments) similarly as if the end effector were a physical object coupled to a physical slave device. Such environments can be used for training surgeons in the use of the hand controllers, in some implementations. In some examples, the user can use or manipulate a master controller to control a proxy visual (e.g., a virtual instrument displayed in a virtual displayed environment, and/or a virtual camera or physical camera included on the slave device or other device), and to control teleoperated surgical arms 1114, 1116, and 1118.

Figure 12:
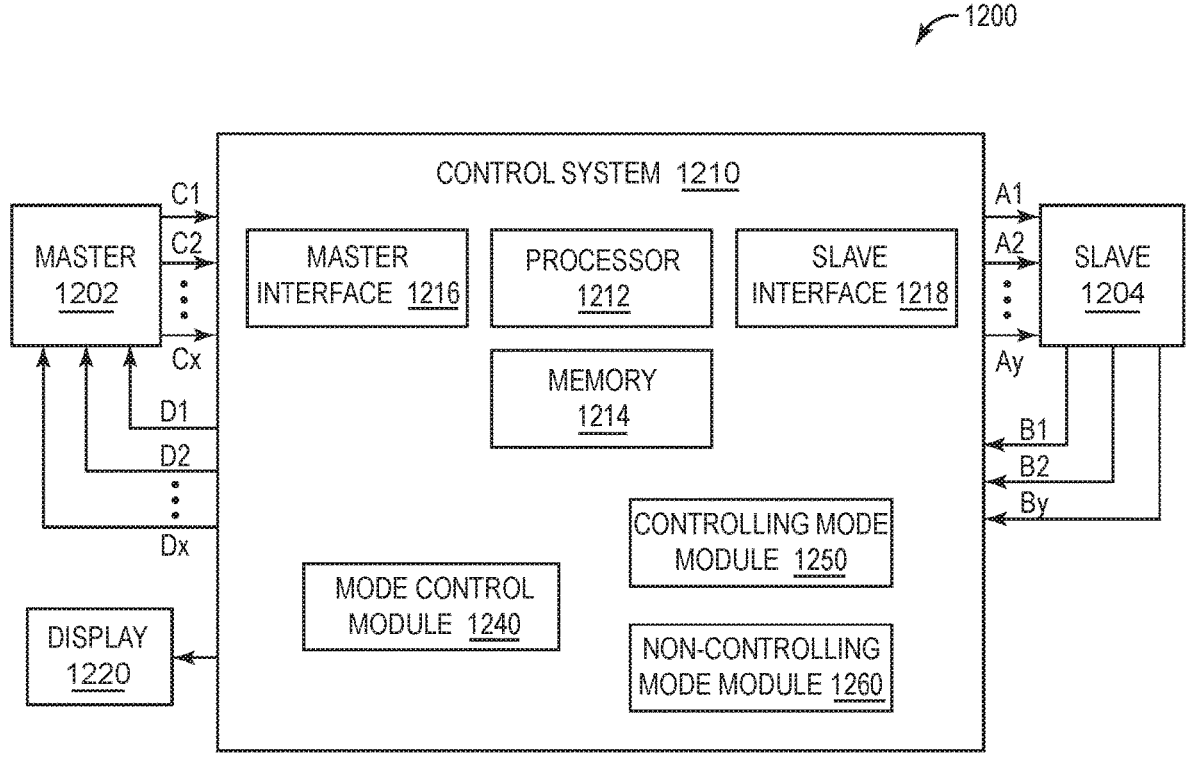
FIG. 12 is a block diagram of an example master-slave system, which can be used for one or more implementations described herein.

FIG. 12 is a block diagram of an example master-slave system 1200, which can be used for one or more implementations described herein. As shown, system 1200 includes a master device 1202 that a user may manipulate in order to control a slave device 1204 in communication with the master device 1202. More generally, master device block 1202 can include one or more of various types of devices providing one or more controllers that can be physically manipulated by a user. For example, master device 1202 can include a system of one or more master controllers such as one or more hand controllers (e.g., master control devices 122 or other hand controllers described herein).

Master device 1202 generates control signals C1 to Cx indicating positions and orientations, states, and/or changes of one or more controllers in their degrees of freedom. For example, the master device 1202 can generate control signals indicating selection of input controls such as physical buttons, hand controller states, and other manipulations of the hand controller by the user.

A control system 1210 can be included in the master device 1202, in the slave device 1204, or in a separate device, e.g., an intermediary device communicatively connected between master device 1202 and slave device 1204. In some implementations, the control system 1210 can be distributed among multiple of these devices. Control system 1210 receives control signals C1 to Cx and generates actuation signals A1 to Ay, which are sent to slave device 1204. Control system 1210 can also receive sensor signals B1 to By from the slave device 1204 that indicate positions and orientations, states, and/or changes of various slave components (e.g., manipulator arm elements). Control system 1210 can include general components such as a processor 1212, memory 1214, and interface hardware 1216 and 1218 such as a master interface and a slave interface for communication with master device 1202 and slave device 1204, respectively. Processor 1212 can execute program code and control basic operations of the system 1200, and can include one or more processors of various types, including microprocessors, application specific integrated circuits (ASICs), and other electronic circuits. Memory 1214 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control system 1210, e.g., one or more displays 1220.

In this example, control system 1210 includes a mode control module 1240, a controlling mode module 1250, and a non-controlling mode module 1260. Other implementations can use other modules, e.g., a force output control module, sensor input signal module, etc. As used herein, the term "module" can refer to a combination of hardware (e.g., a processor such as an integrated circuit or other circuitry) and software (e.g., machine or processor executable instructions, commands, or code such as firmware, programming, or object code). A combination of hardware and software can include hardware only (i.e., a hardware element with no software elements), software hosted by hardware (e.g., software that is stored at a memory and executed or interpreted by or at a processor), or a combination of hardware and software hosted at hardware. In some implementations, the modules 1240, 1250, and 1260 can be implemented using the processor 1212 and memory 1214, e.g., program instructions stored in memory 1214 and/or other memory or storage devices connected to control system 1210.

Mode control module 1240 can detect when a user initiates a controlling mode and a non-controlling mode of the system, e.g., by user selection of controls, sensing a presence of a user using a master controller, sensing required manipulation of a master controller, etc. The mode control module can set the controlling mode or a non-controlling mode of the control system 1210 based on one or more control signals C1 to Cx. For example, mode control module 1240 may activate controlling mode operation if user detection module detects that a user is in proper position for use of the master controller(s) and that signals (e.g., one or more signals C1 to Cx) indicate the user has contacted the master controller(s). The mode control module 1240 may disable controlling mode if no user touch is detected on the master controller(s) and/or if a user is not in proper position for use of the master controller(s). For example, the mode control module 1240 can inform control system 1210 or send information directly to controlling mode module 1250 to prevent the controlling mode module 1250 from generating actuation signals A1 to An that move slave device 1204.

In some implementations, controlling mode module 1250 may be used to control a controlling mode of control system 1210. Controlling mode module 1250 can receive control signals C1 to Cx and can generate actuation signals A1 to Ay that control actuators of the slave device 1204 and cause it to follow the movement of master device 1202, e.g., so that the movements of slave device 1204 correspond to a mapping of the movements of master device 1202. Controlling mode module 1250 can be implemented using conventional techniques.

In some implementations, controlling mode module 1250 can also be used to control forces on the controller(s) of the master device 1202 as described herein, e.g., forces output on one or more components of the master controllers, e.g., hand grip members, using one or more control signals D1 to Dx output to actuator(s) used to apply forces to the components. For example, one or more of control signals D1 to Dx can be output to one or more actuators configured to output forces to one or more hand controllers, actuators configured to output forces on links coupled to a master controller (if it is a mechanically grounded master controller), etc. In some examples, control signals D1 to Dx can be used to provide haptic feedback, gravity compensation, etc.

In some implementations, a non-controlling mode module 1260 may be used to control a non-controlling mode of system 1200. In the non-controlling mode, user manipulations of master device 1202 have no effect on the movement of one or more components of slave 1204. In some examples, non-controlling mode may be used when a portion of slave 1204, e.g., a slave arm assembly, is not being controlled by master device 1202, but rather is floating in space and may be manually moved. For non-controlling mode, non-controlling mode module 1260 may allow actuator systems in the slave 1204 to be freewheeling or may generate actuation signals A1 to An, for example, to allow motors in an arm to support the expected weight of the arm against gravity, where brakes in the arm are not engaged and permit manual movement of the arm. For example, in a medical procedure, non-controlling mode may allow a surgical side assistant to easily manipulate and reposition an arm or other slave component relative to a patient or directly make some other clinically appropriate adjustment of the arm or slave component.

In some implementations, non-controlling mode can include one or more other operating modes of the control system 1210. For example, a non-controlling mode can be a selection mode in which movement of the master controller in one or more of its degrees of freedom and/or selection of controls of the master controller can control selection of displayed options, e.g., in a graphical user interface displayed by display 1220 and/or other display device. A viewing mode can allow movement of the master controller(s) to control a display provided from imaging devices (e.g., cameras), or movement of imaging devices, that may not be included in the slave device 1204. Control signals C1 to Cx can be used by the non-controlling mode module 1260 to control such elements (e.g., cursor, views, etc.) and control signals D1 to Dx can be determined by the non-controlling mode module to cause output of forces on the master controller(s) during such non-controlling modes, e.g., to indicate to the user interactions or events occurring during such modes.

Implementations described herein may be implemented, at least in part, by computer program instructions or code, which can be executed on a computer. For example, the code may be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general-purpose processors, graphics processors, Application Specific Integrated Circuits (ASICs), and the like.

Note that the functional blocks, operations, features, methods, devices, and systems described in the present disclosure may be integrated or divided into different combinations of systems, devices, and functional blocks as would be known to those skilled in the art.

Although the present implementations have been described in accordance with the examples shown, one of ordinary skill in the art will readily recognize that there can be variations to the implementations and those variations would be within the scope of the present disclosure. Accordingly, many modifications may be made by one of ordinary skill in the art without departing from the scope of the appended claims.

What is claimed is:

1. A control device comprising:
 a thumb grip member, a finger grip member coupled to the thumb grip member, a central extension member, an input control, a sensor coupled to at least one of the thumb grip member and the finger grip member, a proximal end, and a distal end opposite the proximal end;
 wherein the thumb grip member comprises a thumb grip receptive to a thumb of a hand of a user of the control device;
 wherein the finger grip member is coupled to the thumb grip member at the proximal end of the control device and extends toward the distal end of the control device;
 wherein the finger grip member comprises a finger grip extension portion and a finger grip receptive to multiple fingers of the hand of the user;
 wherein the finger grip extension portion comprises a first side and a second side reverse of the first side, wherein the finger grip extension portion is configured for contact by at least one of the multiple fingers on the first side of the finger grip extension portion and is configured for contact by a second finger on the second side of the finger grip extension portion;
 wherein the thumb grip member and the finger grip member are moveable in a pinching configuration with reference to each other;
 wherein the central extension member is rigidly coupled to the finger grip member;
 wherein the central extension member moves in accordance with the finger grip member as the finger grip member is moved;
 wherein the central extension member comprises a surface between the finger grip member and the thumb grip member;
 wherein the input control is provided on the surface of the central extension member, the input control operative to sense direct contact of a finger with the input control to provide a control signal to a control system, wherein the input control is selectively accessible to the second finger, wherein the input control is provided on the central extension member in a position to allow the second finger to move between the input control and the second side of the finger grip extension portion; and wherein the sensor is configured to sense relative positions of the thumb grip member and the finger grip member with reference to each other in the pinching configuration.

2. The control device of claim 1, wherein:

the control device is a surgical system control device configured to provide control signals to a surgical teleoperated system.

3. The control device of claim 1, wherein:

the control device comprises a second sensor configured to detect at least one of a position or an orientation of the control device in a working environment of the control device.

4. The control device of claim 1, wherein:

the finger grip receptive to the multiple fingers of the hand has grip space for a maximum of three of the multiple fingers positioned adjacent to each other.

5. The control device of claim 1, wherein:

the thumb grip member and the finger grip member are coupled at the proximal end of the control device to form a single U-shaped unitary piece in which the thumb grip member and the finger grip member are configured to be moved toward or away from each other in the pinching configuration.

6. The control device of claim 5, wherein:

the thumb grip member and the finger grip member are connected by a flexible portion in a central portion of the U-shaped unitary piece.

7. The control device of claim 1, wherein:

the finger grip extension portion extends from the finger grip member in a direction away from the thumb grip member;

the finger grip extension portion is positioned between the multiple fingers and one or more other fingers of the hand; and the finger grip extension portion is configured to be contacted by a second finger of the hand on the second side of the finger grip extension portion.

8. The control device of claim 1, wherein:

the finger grip extension portion is configured to enable the thumb to be disengaged from the thumb grip member during operation of the control device by the hand;

the control device comprises a thumb sensor coupled to the thumb grip member; and the thumb sensor is configured to detect engagement and disengagement of the thumb with the thumb grip member and to provide a thumb sensor signal in response to the engagement or the disengagement.

9. The control device of claim 1, wherein:

the input control is a first input control;

the first side of the finger grip member comprises a finger grip surface contacted by the multiple fingers;

the finger grip member includes an extended portion that extends past the thumb grip member in a direction away from the central extension member;

the control device comprises a second input control coupled to the second side of the finger grip member on the extended portion of the finger grip member; and the second input control is accessible to the thumb of the hand during operation of the control device by the hand, wherein the second input control is operative to sense contact of the thumb with the second input control to provide a second signal to the control system.

10. The control device of claim 1, wherein:

the central extension member is rigidly coupled to the finger grip member, is not coupled to the thumb grip member, and extends from the finger grip member toward the thumb grip member.

11. The control device of claim 1, wherein:

the thumb grip member comprises a thumb grip extension portion that extends from the thumb grip member in a direction away from the finger grip member and that extends at least partially around the thumb.

12. The control device of claim 1, wherein:

the input control is a first input control;

the thumb grip member comprises a first side and a second side reverse of the first side;

a thumb grip surface of the thumb grip is on the first side of the thumb grip member, wherein the thumb grip surface is receptive to the thumb;

the control device comprises a second input control coupled to the thumb grip member on the second side of the thumb grip member; and the second input control is accessible to at least one finger of the multiple fingers of the hand during operation of the control device by the hand, wherein the second input control is operative to sense contact of the second finger with the second input control to provide a second signal to the control system.

13. The control device of claim 1, wherein:

the input control comprises a control wheel positioned between the thumb grip member and the finger grip member; and and the control wheel is configured to output a control signal in response to rotation of the control wheel by at least one finger of the hand or the thumb during operation of the control device by the hand.

14. The control device of claim 1, wherein the input control includes at least one of: a button, a switch, an optical sensor, a capacitive sensor, a pressure sensor, a rocker switch, a control wheel, a dial, a knob, a slider, a trackpad, a joystick, or a trackball.

15. A control device comprising:

a thumb grip member, a finger grip member coupled to the thumb grip member, an input control, a sensor coupled to at least one of the thumb grip member and the finger grip member, a proximal end, and a distal end opposite the proximal end;

wherein the thumb grip member comprises a thumb grip receptive to a thumb of a hand of a user of the control device;

wherein the finger grip member is coupled to the thumb grip member at the proximal end of the control device and extends toward the distal end of the control device;

wherein the finger grip member comprises a finger grip extension portion and a finger grip receptive to multiple fingers of the hand of the user;

wherein the finger grip extension portion comprises a first side and a second side reverse of and opposite to the first side;

wherein the first side of the finger grip member comprises a finger grip surface contacted by the multiple fingers;

wherein the finger grip member includes an extended portion that extends past the thumb grip member in a direction away from the finger grip extension portion;

wherein the thumb grip member and the finger grip member are moveable in a pinching configuration with reference to each other;

wherein the input control is positioned on the second side of the finger grip member on the extended portion of the finger grip member, the input control operative to sense direct contact of the thumb with the input control to provide a control signal to a control system;

wherein the input control is accessible to the thumb of the hand during operation of the control device by the hand; and wherein the sensor is configured to sense relative positions of the thumb grip member and the finger grip member with reference to each other in the pinching configuration.

16. The control device of claim 15, wherein:

the control device comprises a thumb sensor coupled to the thumb grip member; and the thumb sensor is configured to detect engagement and disengagement of the thumb from the thumb grip member and to provide a thumb sensor signal in response to the engagement or disengagement;

in response to detecting the engagement, the thumb sensor signal causes disablement of the input control to send the control signal to the control system; and in response to detecting the disengagement, the thumb sensor signal causes enablement of the input control to send the control signal to the control system.

17. The control device of claim 15, wherein the input control includes at least one of: a button, a switch, an optical sensor, a capacitive sensor, a pressure sensor, a rocker switch, a control wheel, a dial, a knob, a slider, a trackpad, a joystick, or a trackball.

18. A control device comprising:

a thumb grip member, a finger grip member coupled to the thumb grip member, an input control, a sensor coupled to at least one of the thumb grip member and the finger grip member, a proximal end, and a distal end opposite the proximal end;

wherein the thumb grip member comprises a thumb grip receptive to a thumb of a hand of a user of the control device;

wherein the finger grip member is coupled to the thumb grip member at the proximal end of the control device and extends toward the distal end of the control device;

wherein the finger grip member comprises a finger grip extension portion and a finger grip receptive to multiple fingers of the hand of the user;

wherein the finger grip extension portion comprises a first side and a second side reverse of the first side;

wherein the thumb grip member and the finger grip member are moveable in a pinching configuration with reference to each other;

wherein the thumb grip member comprises a first side and a second side reverse of and opposite to the first side;

wherein a thumb grip surface of the thumb grip is on the first side of the thumb grip member, wherein the thumb grip surface is receptive to contact by the thumb;

wherein the input control is positioned on the thumb grip member on the second side of the thumb grip member, the input control operative to sense direct contact of a finger with the input control to provide a control signal to a control system;

wherein the input control is accessible to at least one finger of the multiple fingers of the hand during operation of the control device by the hand; and wherein the sensor is configured to sense relative positions of the thumb grip member and the finger grip member with reference to each other in the pinching configuration.

19. The control device of claim 18, wherein:

the thumb grip member includes a thumb grip extension portion that includes a curving portion that partially curves over the thumb grip member, wherein the input control is positioned on the curving portion.

20. The control device of claim 8, wherein the control device is included in the control system comprising:

a control unit and a controlled device operatively coupled to the control unit;

wherein the control unit is configured to provide control signals to the controlled device;

wherein a first control signal, operative to control a first function of the controlled device, is provided to the controlled device in response to sensing the direct contact by the input control and detection by the thumb sensor of the thumb being engaged with the thumb grip member; and wherein a second control signal, operative to control a second function of the controlled device, is provided to the controlled device in response to sensing the direct contact by the input control and detection by the thumb sensor of the thumb being disengaged with the thumb grip member.

* * * * *